United States Patent
Marangoni et al.

(10) Patent No.: US 11,834,694 B2
(45) Date of Patent: Dec. 5, 2023

(54) STRUCTURAL LIPIDS

(71) Applicant: Planted Foods AG, Kemptthal (CH)

(72) Inventors: Alejandro G. Marangoni, Guelph (CA); Reed A. Nicholson, Guelph (CA)

(73) Assignee: Planted Foods AG, Kemptthal (CH)

( * ) Notice: Subject to any disclaimer, the term of this patent is extended or adjusted under 35 U.S.C. 154(b) by 48 days.

(21) Appl. No.: 17/403,297

(22) Filed: Aug. 16, 2021

(65) Prior Publication Data

US 2023/0057409 A1     Feb. 23, 2023

(51) Int. Cl.
| | | |
|---|---|---|
| C12P 7/6409 | (2022.01) | |
| C11C 3/06 | (2006.01) | |
| A23L 33/12 | (2016.01) | |
| C07C 69/00 | (2006.01) | |

(52) U.S. Cl.
CPC ............ *C12P 7/6409* (2013.01); *A23L 33/12* (2016.08); *C07C 69/00* (2013.01); *C11C 3/06* (2013.01); *C12Y 301/01003* (2013.01)

(58) Field of Classification Search
CPC ..... C12P 7/6409; C12P 7/6445; C12P 7/6458; C07C 69/66; C12Y 301/01003; C11C 3/06
See application file for complete search history.

(56) References Cited

U.S. PATENT DOCUMENTS

| | | | |
|---|---|---|---|
| 6,369,252 B1 * | 4/2002 | Akoh | ................. A61K 38/465 435/135 |
| 7,452,702 B2 | 11/2008 | Lee | |
| 8,663,628 B2 | 3/2014 | Soe | |
| 2004/0091574 A1 | 5/2004 | Soe | |
| 2005/0014237 A1 | 1/2005 | Lee | |
| 2008/0233235 A1 | 9/2008 | Soe | |
| 2017/0112159 A1 * | 4/2017 | Grimaldi | ................ A61Q 19/00 |

FOREIGN PATENT DOCUMENTS

WO    2018206464 A1    11/2018

OTHER PUBLICATIONS

Subroto E., Monoacylglycerols and diacylglycerols for fat-based food products: a review, Food Research 4(4), pp. 932-943 (Year: 2020).*

Vu, P.L., et al., Two-step production of oil enriched in conjugated linoleic acids and diacylglycerol, J. Amer. Oil Chem. Soc., 84, pp. 123-128 (Year: 2006).*

(Continued)

*Primary Examiner* — Yate' K Cutliff
(74) *Attorney, Agent, or Firm* — Nelson Mullins Riley & Scarborough LLP; Jane E. Remillard, Esq.; Jill Gorny Sloper, Esq.

(57) ABSTRACT

An enzymatic glycerolysis method to convert an oil having a first monoacylglycerol (MAG), diacylglycerol (DAG), triacylglycerol (TAG) and fatty acid composition into a structured fat is provided. The method comprising the steps of exposing the oil to glycerol in the presence of an enzyme catalyst under conditions sufficient to convert the triacylglycerols to mono- and/or di-acylglycerols; and cooling the oil to yield the structured fat having a second monoacylglycerol, diacylglycerol, triacylglycerol and fatty acid composition, wherein the fatty acid composition of the oil is essentially retained in the structured fat. The structured fat provides a healthy substitute for saturated fats in foods.

18 Claims, 17 Drawing Sheets

(56) References Cited

OTHER PUBLICATIONS

Vazquez. L., et al., A first attempt into the production of acylglycerol mixtures from Echium oil, Frontiers in Bioengineering and Biotechnology, vol. 3, article 208, pp. 1-11 (Year: 2016).*
Reed A. Nicholson and Alejandro G. Marangoni—"Enzymatic Glycerolysis Converts Vegetable Oils into Structural Fats with the Potential to Replace Palm Oil in Food Products", Nature Research 2020.
Reed A. Nicholson and Alejandro G. Marangoni—"Lipase-catalyzed Glycerolysis Extended to the Conversion of a Variety of Edible Oils into Structural Fats", Current Research in Food Science 4 (2021) 163-174.
Vereecken et al.—"Fat Structuring with Partial Acylglycerols: Effect on Solid Fat Profiles", Eur. J. Lipid Sci. Technol. 2009, 111, 259-272.
Meghwanshi et al.—"Characterization of 1,3-Regiospecific Lipases fro New Pseudomonas and BacillusIsolates", Journal of Molecular Catalysis B: Enzymatic 40 (2006) 127-131.
Nicholson, R.A., and Marangoni, A.G. (2019) Diglycerides in Melton, L., Shahidi, F., Varelis, P. (Eds), Encyclopedia of Food Chemisty, vol. 1, Elsevier, pp. 70-73.
Nicholson, R.A., and Marangoni, A.G. (2020) Food structure development in oil and fat systems In: Spyropoulos, F., Lazidis, A. Norton, I. (Eds), Handbook of Food Structure Development, first ed., Royal Society of Chemistry, pp. 115-133.
Vereecken J, et al.—"Fat Structuring with Partial Glycerides: Effect on Solid Fat Profiles," Laboratory of Food Technology and Engineering, pp. 1-42 (2010).

* cited by examiner

STRUCTURAL LIPIDS

FIELD OF THE INVENTION

The present invention generally relates to glycerolysis of liquid oils, and in particular, to structural fats prepared by glycerolysis of liquid oils.

BACKGROUND

Partially hydrogenated oils were banned from food products in both Canada and the USA in 2018 due to their high content of trans fatty acids which have been known to have negative effects on serum cholesterol levels for many years (Katan et al., 1995). Even before this ban was announced, many food companies had begun looking for alternatives to trans fats. This led to major growth in the field of fat mimetics (Marangoni et al., 2019; Patel et al., 2020). Many different fat mimetic strategies have been explored thus far. These can be categorized as mono and mixed component oleogels, structured biphasic systems, and polymer oleogels (Marangoni et al., 2019). Several strategies have shown success, but they have yet to be used by the food industry on a large scale basis. Instead, saturated fat sources remain the primary means of replacing the partially hydrogenated oils. These saturated fat sources are mainly palm oil (along with an increasing prevalence of coconut oil) or fully hydrogenated vegetable oils (e.g. soybean and rapeseed oils), which are then typically interesterified with a liquid vegetable oil, producing a fat with an intermediate level of solids.

Saturated fat consumption has been linked to coronary heart disease. The history of the study of saturated fat consumption and its relation to coronary heart disease was well summarized by Marangoni and coworkers (2019). On the other hand, unsaturated fatty acid consumption was found to have a positive effect on cholesterol levels (a risk factor for coronary heart disease) compared to saturated fatty acid consumption, and reduced saturated fatty acid contents along with increased unsaturated fatty acids contents was considered to provide beneficial health effects. Nevertheless, since many of the previously investigated low-saturated fatty acid fat mimetic strategies have yet to be implemented on a large scale by the food industry, an effective strategy for converting liquid oils, high in the more desirable unsaturated fatty acids, into structural fats remains outstanding.

Partial acylglycerols, including mono- and diacylglycerols (MAGs and DAGs), are commonly used emulsifiers in the food industry, and are frequently used in bakery products, frozen desserts, and sauces/dressings. The MAG molecule has two free hydroxyl groups while DAG molecules contain only one. As a result, MAGs are more hydrophilic compared to DAGs and have a higher hydrophilic-lipophilic balance (HLB) value. In addition, MAGs have a greater surface activity relative to DAGs, rendering them a more sought-after emulsifier ingredient. However, due to the expense involved in completely separating the partial acylglycerols through distillation processes, mixtures of MAGs and DAGs are usually used. This can be beneficial as emulsifiers with differing HLB values, e.g. a mixture of MAGs and DAGs, may perform better than MAGs alone.

In addition to partial acylglycerols being used commonly as emulsifiers, DAG oil (oil containing approximately 80% DAGs, compared to less than 10% DAGs in conventional cooking oils) was commercialized previously, and provided health benefits over triacylglycerol-containing oils (TAGs) such as reduced serum TAG levels, body fat stores, body mass index, waist circumference, low-density lipoprotein cholesterol levels, and total cholesterol levels along with increased high-density lipoprotein cholesterol levels. These health benefits result since 1,3-DAGs cannot be metabolized through the same pathway as TAGs.

Partial acylglycerols can be produced through a variety of processes, however, MAGs and DAGs for commercial use are typically produced through either a direct esterification of fatty acids onto glycerol or a glycerolysis reaction between glycerol and a fat or oil blend. Glycerolysis is more cost-effective than the esterification route because glycerol is required in lower quantities and the cost of fatty acids is greater than that of the fat or oil. Both processes can be performed chemically or enzymatically. Reactions catalyzed chemically are generally more economical, faster, and more consistent, however, they must be performed at higher temperatures (>200° C.) leading to oxidative degradation of the oils and possibly the production of 3-monochloropropane-1,2-diol and glycidyl esters, which are known to be produced when partial acylglycerols react with chlorine above 160° C. Since enzymatic glycerolysis is performed at lower temperatures (50-80° C.), preserving oil quality, and the use of biocatalysts is considered to be more eco-friendly than use of chemical catalysts, enzymatic glycerolysis is an attractive method to produce MAGs and DAGs. Due to the frequent use of MAGs and DAGs as food ingredients and the overall effectiveness of enzymatic glycerolysis as a means of production, research has been performed to improve the partial acylglycerol yields of enzymatic glycerolysis (McNeill et al., 1991; Noureddini and Harmeier, 1998; Elfman-Borjesson and Harrod, 1999; Kristensen et al., 2005; Fregolente et al., 2008).

Structural differences between MAGs, DAGs, and TAGs, other than the surface-active properties that come from the free hydroxyl groups on partial acylglycerol molecules, means that these molecules crystallize differently. TAGs can crystallize into three polymorphic forms based on the subcell packing arrangement of the fatty acid chains. The α form (hexagonal subcell) is the least stable, followed by the β' (orthorhombic perpendicular subcell) form. The β (triclinic subcell) packing arrangement is the most stable, has the greatest subcell density, and the highest melting point of the three forms. MAGs exist as either 1-MAG or 2-MAG positional isomers with 1-MAG begin the more common form, representing ~90 wt % of MAGs. MAGs also demonstrate α, β', and β polymorphic forms, along with a metastable sub-α polymorphic form, which has a reversible transformation temperature below the α polymorphic form. DAGs exist as two positional isomers, 1,2-DAG and 1,3-DAG, at an equilibrium of 30-40:60-70 mol:mol. A hairpin configuration is adopted by the 1,2-DAGs and they crystallize in either the α-form or β'-form, while 1,3-DAGs adopt a V-shaped configuration and can crystallize into either a lower-melting β2 polymorph or a higher-melting β1 polymorph. When the acylglycerol molecules are in their most stable polymorphic form, the crystal packing arrangement variations produce differences in the crystallization and melting temperatures between the molecules even if the same fatty acids are present. For example, if palmitic acid is bound to the glycerol molecule, β form tripalmitin melts at 65.5° C., while the β1 polymorph of 1,3-dipalmitoyl-glycerol melts at 73.0° C., and the β' polymorph of 1,2-dipalmitoyl-glycerol melts at 67.5° C. In contrast, the β form of 1-monopalmitin melts at 77.0° C. As a result, MAGs have the highest melting point, followed by 1,3-DAGs. In this instance, the 1,2-DAG melting point is higher than that of the TAG, however, these melting points are often relatively similar.

Due to the higher crystallization and melting points of MAGs and DAGs, the impact of these molecules on the crystallization behaviour of TAGs has received attention over the past two decades. In some cases, the effect of partial acylglycerols on TAG crystallization may be positive. For example, saturated MAGs (monopalmitin and monostearin) have been shown to act as a template for TAG nucleation, increasing the onset of crystallization temperature and enhancing crystal growth. Saturated DAGs (dipalmitin and distearin), as well as diolein at low addition levels, were shown to accelerate triolein crystallization. In addition, 1-palmitoyl-2-oleoyl-glycerol accelerated nucleation and crystal growth of milk fat TAGs. However, partial acylglycerols may also have negative implications on crystallization. For example, diolein, dipalmitin, and distearin were shown to delay the crystallization onset of tripalmitin and tristearin when incorporated at 5%. In addition, 1, 2, and 4% saturated MAGs (monopalmitin and monostearin) delayed the onset of crystallization of DAGs (20 wt % dispersed in sunflower oil) containing primarily palmitic and stearic acids.

The use of MAG-DAG blends as a means of increasing the solid fat content (SFC) of vegetable oils was first introduced by Vereecken and coworkers (2009). In these MAG-DAG blends, MAGs were shown to raise the SFC of the mixtures to a greater extent than DAGs, and higher contents of saturated MAGs maintained a higher SFC as the sample temperature was increased. While these partial acylglycerol blends were never used to structure a liquid oil, the melting point of rapeseed oil was increased through the addition of a commercial MAG composed primarily of monostearin.

It would be desirable, thus, to develop structural fats that are a healthier alternative to saturated fats.

SUMMARY

An enzymatic glycerolysis method has now been developed to convert liquid oils into a novel structural fat that retains the fatty acid composition of the liquid oil.

Thus, in one aspect, an enzymatic glycerolysis method is provided to convert an oil having a first monoacylglycerol, diacylglycerol, triacylglycerol and fatty acid composition into a structured fat, the method comprising the steps of: i) exposing the oil to glycerol in the presence of an enzyme catalyst under conditions sufficient to convert the triacylglycerols to mono- and/or di-acylglycerols; and ii) cooling the oil to yield the structured fat having a second monoacylglycerol, diacylglycerol, triacylglycerol and fatty acid composition, wherein the fatty acid composition of the oil is essentially retained in the structured fat.

In another aspect, a structured fat obtained by glycerolysis of a liquid oil is provided comprising 10-50% monoacylglycerols (MAGs), 30-70% diacylglycerols (DAGs) and 5-40% triacylglycerols (TAGs).

In another aspect, a structured fat obtained by glycerolysis of a liquid oil is provided, wherein the oil comprises a first MAG, DAG, TAG and fatty acid composition, and the structured fat product comprises a second MAG, DAG, TAG and fatty acid composition, wherein the fatty acid composition of the oil is essentially retained in the structured fat.

These and other aspects of the invention are described by reference to the following figures.

DETAILED DESCRIPTION

Figure 1:
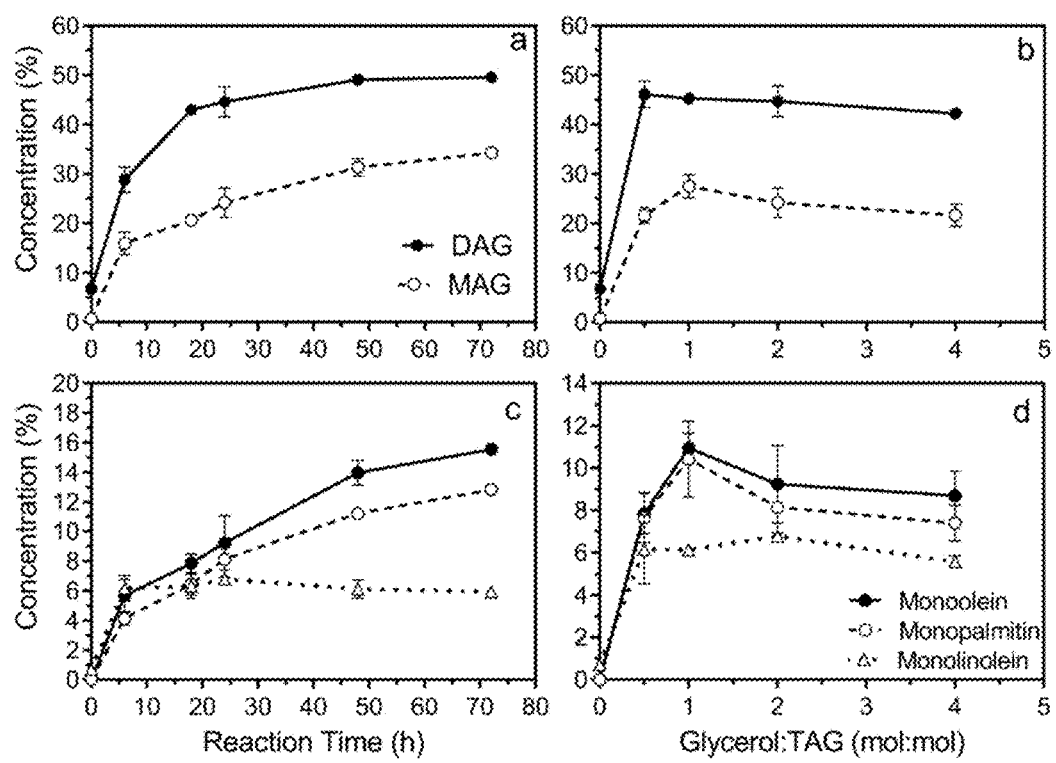
FIG. 1 graphically illustrates the partial glycerol contents in glycerolysis reaction products including changes in total MAG and DAG concentrations during glycerolysis of cottonseed oil as a function of reaction time at a 2:1 glycerol:TAG molar ratio (a) and at different glycerol:TAG molar ratios after 24 h reaction time (b), and changes in the concentrations of the major MAG species as a function of reaction time (c) and at different glycerol:TAG molar ratios (d). Values represent the means and standard deviations (error bars) of three replicates.

In one aspect, an enzymatic glycerolysis method is provided to convert an oil having a first monoacylglycerol, diacylglycerol, triacylglycerol and fatty acid composition into a structured fat. The method comprises the steps of: i) exposing the oil to glycerol in the presence of an enzyme catalyst under conditions sufficient to convert the triacylglycerols to mono- and/or di-acylglycerols; and ii) cooling the oil to yield the structured fat having a second monoacylglycerol, diacylglycerol, triacylglycerol and fatty acid composition, wherein the fatty acid composition of the oil is essentially retained in the structured fat.

The present method is useful to convert liquid oils into a structured fat product. Oils for conversion into a structured fat product, include, but are not limited to, vegetable oils such as sunflower oil, canola oil, safflower oil, soybean oil, avocado oil, olive oil, corn oil, flaxseed oil, almond oil, coconut oil, peanut oil, pecan oil, cottonseed oil, algal oil, palm oil, palm olein, palm kernel oil, rice bran oil, sesame oil, butteroil, grape seed oil, hazelnut oil, brazil nut oil, linseed oil, acai palm oil, passion fruit oil, walnut oil, tigernut oil, shea olein, palm kernel olein, and mixtures thereof. As one of skill in the art will appreciate, suitable oils will vary with respect to their acylglycerol content, including mono-, di- and tri-acylglycerol contents. For example, oils having increased oleic acid content, may also be used including high oleic acid-containing oil such as high-oleic sunflower, high-oleic soybean, high-oleic canola, high-oleic safflower oil, and mixtures thereof. The term "high-oleic acid" refers to an oil containing an increased amount of oleic acid as compared to the typical oleic acid content of the oil. This increase may be a 20% or more increase in oleic acid content from the typical amount in a given oil. Other liquid oils may used, including animal oils, e.g. chicken fat or emu oil. An oil for use in the present method is liquid at temperatures above 4° C.

The method is conducted by exposing the selected oil to glycerol in the presence of an enzyme catalyst. The method may be conducted with variable amounts of glycerol. The amount of glycerol to be utilized in the present glycerolysis reaction is generally determined based on the TAG content of the oil. In an embodiment, the method is conducted with an amount of glycerol relative to the TAG content of the oil in the range of about 0.25-4:1, for example, 0.5-2:1, and preferably, 0.5-1:1 glycerol:TAG (mol:mol).

The enzyme catalyst for use in the present method is any enzyme that can catalyze glycerolysis, i.e. hydrolyze triacylglycerols and re-esterify them onto the free glycerol backbone molecule. Examples of suitable enzymes include, but are not limited to, lipases, including both non-specific lipases and sn-1,3 specific lipases which hydrolyse/esterify fatty acid specifically at either or both of the sn-1 and sn-3 positions. Examples of lipases for use include human pancreatic lipase, and lipases obtained from fungi, yeast and bacteria, e.g. *Aspergillus niger, Rhizomucor delemar, Rhizomucor miehei, Mucor javanicus, Candida* sp. such as *C. antarctica* and *C. rugosa, Pseudomonas* sp., and *Bacillus subtilis*, which may be either specific or non-specific. Such enzymes are generally commercially available. For use in the glycerolysis reaction, the selected enzyme will generally be immobilized on a solid support such as a polymeric support, e.g. bead, resin or silica. Immobilization may be achieved via adsorption of the enzyme onto the solid support or by covalent linkage of the enzyme to the polymer support. The enzyme is utilized in an amount sufficient to catalyze the glycerolysis reaction, which may vary with the enzyme and the oil used in the reaction. Generally, enzyme in an amount ranging from about 1-10% by weight of the oil is used in the glycerolysis reaction. In an embodiment, for example, an amount of non-specific lipase, e.g. such as lipase from *C.*

*antarctica*, of up to about 5% by weight of the oil, such as an amount of 1-4% by weight of the oil, e.g. about 2% by wt of the oil, is utilized.

The conditions used to conduct the glycerolysis reaction are selected based on the oil and enzyme catalyst employed. For example, reaction temperature is selected so as to avoid or minimize enzyme denaturation. Suitable temperatures may range from about 40° C. to about 80° C. Similarly, the length of the reaction will vary on the oil and enzyme used. Reaction times may vary from about 1 to about 48 hours or longer. Generally, glycerolysis in accordance with the present method is substantially complete within about 24-48 hours. The phrase "substantially complete" as used herein with respect to completion of the glycerolysis reaction refers to about 90-95% conversion of TAGs to MAGs and/or DAGs.

Once glycerolysis has been conducted to completion or near completion, the temperature of the reaction mixture is cooled to a temperature which yields a structured fat product. The term "structured" or "structural" is used herein to refer to a fat product having particular physical and chemical properties. The structuring power of the present glycerolysis reaction is due to the altered crystallization and melting behavior of the oils resulting from the production of mono- and diacylglycerols (MAGs and DAGs) from component triacylglycerols (TAGs). This results in an increased level of crystallization and higher melting points as a result of the higher MAG and DAG (particularly 1,3-DAGs) content in the structured fat as compared to TAG content, while the fatty acid composition is essentially unaltered.

Thus, a structured fat in accordance with aspects of the invention, comprises a fat product having a MAG and DAG content that is increased, and/or a TAG content that is decreased, in comparison to the MAG/DAG and TAG content, respectively, of the starting oil material or native oil (including oil mixtures) that is subjected to enzymatic glycerolysis in accordance with the present method. The MAG, DAG and TAG content of the structured fat product is such that it yields a product that exhibits an increase in solid fat content (SFC) as compared to the native oil, but in which the average fatty acid content is essentially consistent with the native oil.

The structured fat resulting from the present glycerolysis method comprises a MAG content which is at least 10% greater than the MAG content of the native oil, and a DAG content which is at least 10% greater than the DAG content of the native oil. In embodiments, the MAG content of the structured fat is at least 15%, 20%, 25%, 30% or greater, than the MAG content of the native oil. In embodiments, the DAG content of the structured fat is at least 15%, 20%, 25%, 30%, 35%, 40% or greater, than the DAG content of the native oil. As one of skill in the art will appreciate, native oils such as vegetable oils will generally comprise little or no MAGs or DAGs, e.g. less than 1% MAGs and less than 10% DAGs, and thus, substantially consist of TAGs.

The structured fat resulting from the present glycerolysis method comprises a TAG content which is at least 20% less than the TAG content of the native oil. In embodiments, the TAG content of the structured fat is reduced by at least 25%, 30%, 40%, 50%, 60%, 70% or more, as compared to the TAG content of the native oil.

Thus, the present glycerolysis structured fat comprises about 10-50% monoacylglycerols (MAGs) and about 30-70% diacylglycerols (DAGs), that form about 60-95% of the acylglycerol content of the structured fat, and, thus, comprises about 5-40% triacylglycerols (TAGs). As one of skill in the art will appreciate, the MAG, DAG and TAG content will vary within these ranges based on the native oil, the enzyme used to conduct the glycerolysis reaction, and the reaction conditions. In embodiments, the DAG content is greater than the MAG content in the structured fat, for example, the DAG content is at least 10%, 15%, 20% or more, greater than the MAG content.

The MAG and DAG content of the present structured fat product may comprise saturated and unsaturated monoacylglycerols and diacylglycerols, respectively. In one embodiment, the MAG content comprises 3-30% saturated monoacylglycerols and 70-97% unsaturated monoacylglycerol.

It is notable that, in accordance with the present glycerolyis method, oils are converted into structured fats which essentially retain the average fatty acid composition of the native oil. The term "essentially" as used herein with respect to the retention of the average fatty acid composition of the structured fat refers to the retention of at least about 95% of the fatty acid composition of the native oil within the structured fat, and preferably retention of greater than 95%, i.e. 96%, 97%, 98%, 99%, or 100%, of the average fatty acid composition of the native oil within the structured fat.

The increased MAG and DAG content of the structured fat desirably results in an increased solid fat content of the structured fat without an increase in saturated fats, i.e. a solid fat content of at least about 5% greater than the solid fat content of the native oil, including a solid fat content of at least about 10%, 15%, 20%, 25%, 30% or more, greater than the solid fat content of the native oil, at a given temperature. In embodiments of the invention, the structured fat has a solid fat content of at least about 15% at 5° C., and preferably at least about 20% at 5° C. In other embodiments, the structured fat has a solid fat content of at least about 5% at 20° C., and preferably at least about 10% at 20° C.

Solid fat content of the structured fat varies based on the native oil and the conditions of the glycerolysis reaction. Generally, conditions which result in a higher conversion of TAG to MAG and/or DAG, will result in a structured fat product with a higher solid fat content. In this regard, glycerol content in the reaction mixture may be varied to alter solid fat content. For example, the use of glycerol in a molar ratio of 0.5-2:1 glycerol:TAG (mol:mol) results in higher solid fat contents, with a 1:1 ratio of glycerol:TAG yielding a structured fat with the highest solid fat content for a given oil/enzyme system.

Solid fat content also varies with the specificity of the enzyme utilized in the glycerolysis reaction. Non-specific lipases will generally yield a higher rate of TAG conversion to MAGs and DAGs, given that they are able to hydrolyze at each of the sn-1, sn-2 and sn-3 positions of TAG, whereas specific lipases hydrolyze at the sn-1 and sn-3 positions, and not the sn-2 position, of TAG.

As one of skill in the art will appreciate, the solid fat content of the structured fat will vary with temperature, i.e. solid fat content decreases as temperature increases. Preferably, the present structured fat will generally have a solid fat content that renders it to be a solid or semi-solid at a temperature of about 20-25° C., i.e. about room temperature, and which permits melting at higher temperatures, e.g. about 30-50° C. This will provide a structured fat that substantially melts when consuming, and avoids or at least reduces an undesirable waxy mouthfeel during consumption.

Thus, the present method permits the production of a structured fat designed to imitate the features of a target product with respect to solid fat content, e.g. consistency and melting point, to yield a product having the desired properties.

The physical characteristics of the structured fat are based on the crystal network that forms following glycerolysis. While the crystal network varies in glycerolysis structured fats produced from different oils, the crystal network formed in each case exhibited a crystallization onset at a temperature of at least 10° C. higher, e.g. 15° C., 20° C., or higher, than that of the native oil from which it was produced, and results in a microstructure with enhanced oil-binding capacity, i.e. with reduced oil loss of at least about 20%, 30%, 40%, 50%, or more, as compared to the native oil.

In another aspect of the invention, a food product is provided comprising the glycerolysis structured fat. The structured fat may be readily used to replace fat-based products such as butter, margarine, shortening, dressings, spreads, and the like. Thus, the structured fat may be used for cooking of any product in place of butter, margarine or oils are used, including cooking of meat, sauces, gravy, etc., as well as a topping on breads or other baked goods, vegetables, pasta, rice, etc. It is also useful to replace butter, margarine or oils in baked goods such as breads, cakes, cookies, etc., and confections. The structured fat may also be used to make spreads such as nut butters (e.g. peanut butter, almond butter, etc.), pastes, frosting, creams, toppings, and the like.

As one of skill in the art will appreciate, the structured fat may be combined with one or more additional ingredients to more closely simulate a target food product. For example, for use as a replacement for a fat or oil, such as butter or margarine, the structured fat may include ingredients such as water, flavouring agents, colouring agents, antioxidants, preservatives, nutrients, etc. Similar ingredients are added to make dressings, spreads and the like.

Flavouring agents may include salt, sweetening agents, spices, herbs, simulated flavours, and the like.

Examples of preservatives that may be used include, but are not limited to, sodium benzoate, sodium and calcium propionate, sorbic acid, ethyl formate, and sulfur dioxide.

Examples of anti-oxidants that may be used include, but are not limited to, ascorbic acid, tocopherols, butylated hydroxyanisole and propyl gallate.

Nutrients that may be combined with the structured fat include vitamins (e.g. vitamin A, C, E, K, D, thiamin (vitamin B1), riboflavin (vitamin B2), niacin (vitamin B3), vitamin B6, folic acid (vitamin B9) and/or vitamin B12, and mixtures thereof), minerals (e.g. calcium, phosphorus, magnesium, sodium, potassium, chloride, iron, zinc, iodine, selenium, copper and mixtures thereof), and protein isolates such as pea protein, soy protein, fava protein, yeast protein and other organisms, corn protein, wheat protein, rice protein, canola protein, peanut protein, bean protein, lentil protein, pumpkin seed, rice, brown rice, peanut, almond, chia seed, flax seed and combinations thereof. The protein source may be non-hydrolyzed, partially hydrolyzed or hydrolyzed and may be in the form of an intact protein, amino acid or peptide.

Additional ingredients that may be included in food products made with the structured fat include fillers, bulking or thickening agents and plasticizing agents.

Examples of fillers to provide volume/bulk while not impacting desired properties, such as rheological melting properties, include, but are not limited to, consumable inert components such as microcrystalline cellulose, maltodextrin, dextrin, pea protein, soy protein, inulin, sugars and mixtures thereof.

Examples of thickening and/or gelling agents include, but are not limited to, starches such as arrowroot, cornstarch, katakuri starch, potato starch, sago, wheat flour, almond flour, tapioca and starch derivatives; modified or pre-gelatinized starches, microbial and vegetable gums such as alginin, guar gum, locust bean gum, gellan gum, tara gum, Arabic gum, Konjac and xanthan gum; proteins such as collagen, egg white and gelatin; or sugar polymers such as agar, carboxymethyl cellulose, pectin and carrageenan (e.g. kappa, iota, lambda); and mixtures thereof.

Examples of food grade plasticizers include, but are not limited to, food grade acids such as levulinic acid, palmitic acid, stearic acid, and oleic acid, food grade carboxylic acids, such as citric, malic, lactic, acetic, oxalic and tartaric acid, glycerol, polyethylene glycol, triethylene glycol, ethylene glycol, sorbitol, sugars such as fructose, galactose and glucose, and mixtures thereof.

In one embodiment, the structured fat is used to make a meat substitute. The structured fat is combined with a suitable protein, such as a plant-based protein, filler, water and flavouring agents to yield a meat substitute having suitable hardness (N), springiness, cohesiveness, resilience and cook loss properties.

The glycerolysis structured fat may also be used in cosmetic and/or health care products for skin and hair. For example, the structured fat may be used to make creams, lotions, body butters, conditioning products, and other products which require structuring. In this case, the structured fat forms the base of the product, and is combined with the active ingredients and ingredients otherwise included within the cosmetic or health care product.

The present glycerolysis method provides a strategy to convert liquid oils into structural fats having properties which render them to be advantageous, particularly for use in food applications. The structured fats are useful to replace palm oil and hydrogenated fats in food products to provide a healthy alternative in which monounsaturated and polyunsaturated fatty acids are increased, but saturated fatty acids is decreased. Consumption of foods prepared with such a structured fat will, thus, have beneficial effects on health and well-being by aiding in the reduction of serum cholesterol levels and promote cardiovascular health.

Embodiments of the invention are described by reference to the following specific Examples which are not to be construed as limiting.

Example 1—Enzymatic Glycerolysis to Convert Vegetable Oils into Structural Fats

An enzymatic glycerolysis method was developed to convert vegetable oils into structural fats as described.

Methods and Materials

Materials—Cottonseed oil was purchased online (Bass Pro Shops). Glycerol (99.9% glycerol, Fisher Scientific) was obtained through a scientific material supplier. *C. antarctica* lipase B immobilized on Immobead 150 was purchased from Sigma-Aldrich.

Glycerolysis Reaction—Glycerolysis reactions were performed with cottonseed oil as the substrate. Using a 125 ml Erlenmeyer flask as the reaction vessel, glycerol was added to the oil (30 g) at various molar ratios (0.10:1, 0.25:1, 0.5:1, 1:1, 2:1, 4:1) of glycerol to TAG. The mass of glycerol reacted was determined based on the molecular weights of the glycerol and TAG molecules. Glycerol has a molecular weight of 92 g mol$^{-1}$, while the TAG molecular weight ($M_w$) was calculated using the equation: $M_w=3\times(56,000/SV)$, where SV represents the saponification value of the cottonseed oil. A saponification value of 194 was used. Furthermore, deionized water was added at a concentration of 3.5 wt % relative to the glycerol. *C. antarctica* lipase B, immobilized on Immobead 150, was added at 2 wt % relative to the oil. The flask was lightly shaken by hand to disperse the enzyme particles within the mixture immediately before placing this in a shaking water bath (Precision Reciprocal Shaking Bath, ThermoScientific). With the water bath set to a temperature of 65° C. and a reciprocating speed of 130 rpm., glycerolysis reactions were run for various times (6, 18, 24, 48 and 72 h). Glycerolysis reactions performed with each of the different glycerol ratios were run for 24 h, while a glycerol:TAG molar ratio of 2:1 was used for the glycerolysis reactions that were run for the various times. Reactions were performed under various conditions to maximize the structuring capabilities achievable at the 2 wt % lipase concentration used. Upon completion of the reaction, the contents were centrifuged (Model CL, International Equipment) for 5 min at 495 g to separate the oil from the immobilized lipase, glycerol and water.

Fatty Acid Composition—The fatty acid composition of the oils was determined with an Agilent 6890-series gas chromatograph (Agilent Technologies) equipped with a 7683-series autosampler. A BPX70 (SGE) gas chromatograph column (60 m×0.22 mm internal diameter; 0.25 µm film thickness) was used. The oven temperature increased from 110 to 230° C. (4° C. min$^{-1}$) and then maintained at 230° C. for 18 min. The injector was set to 250° C., operating at 20.1 p.s.i. and a flow of 17.7 ml min$^{-1}$. The carrier gas (high-purity helium) was set to flow at a velocity of 25 cm s$^{-1}$. A flame ionization detector was used (255° C.; 450 ml min$^{-1}$ airflow; 50 ml min$^{-1}$ helium flow). The gas chromatograph peaks were analysed with Open LAB software (Agilent Technologies). Retention times of internal standards were used to determine the fatty acid composition.

SFC Melting Profile—SFC was measured using pulsed NMR (minispec mq20, Bruker) at temperatures between 5 and 50° C. with 5° C. intervals (AOCS Official Method Cd 16b-93). Samples were transferred to standard NMR tubes (height, 180 mm; diameter, 9 mm) and stored at 5° C. for 1 week before performing measurements.

Determination of MAG and DAG Contents—The MAG and DAG contents were determined with a Waters 2690 Alliance HPLC system (Waters) equipped with a Waters 2410 refractive index detector. Chromatographic separation of the MAGs, DAGs, and TAGs in the samples was achieved with a Waters xbridge C18 column (4.6 mm×250 mm internal diameter; 5 µm particle size). Isocratic elution at a flow rate of 1 ml/min$^{-1}$ of degassed acetone/acetonitrile 60/40 (vol/vol) was applied. Column and detector temperatures were set to 40° C. The data obtained were analysed using Millenium32 Chromatography Manager software (Waters).

Differential Scanning calorimetry—Differential scanning calorimetry (DSC 1 Star System, Mettler Toledo) was used to investigate the crystallization behaviour of the products of each of the glycerolysis reactions. Between 8 and 10 mg of sample was placed in aluminium crucibles that were hermetically sealed before testing. Samples were first heated to 100° C. and held for 15 min to ensure the crystal structure was completely melted. Crystallization was investigated by cooling the samples to −80° C. at a rate of 5° C. min$^{-1}$.

Accelerated Oil Loss—The accelerated oil loss of the samples was investigated via centrifugation. Portions (1 g) of the sample were crystallized and stored at 5° C. for at least 24 h in 2 ml microcentrifuge tubes. The centrifugation unit (4515, Eppendorf) was equilibrated in a refrigerator (5° C.) before testing. Samples were centrifuged for 1 h at 16,110 g. Following centrifugation, the weight of the expelled oil was determined. The amount of oil loss was reported as a percentage weight loss relative to the initial weight of the sample.

Polarized Light Microscopy—The sample microstructure was characterized by polarized light microscopy under a digital plan trinocular infinity polarizing laboratory microscope (M838PL-C180U3, OMAX). Before imaging, previously prepared samples were melted and transferred to glass microscope slides stored at 40° C. Glass coverslips (40° C.) were then placed over the samples which were stored at 5° C. for 1 week. The sample temperature during imaging was maintained at 5° C. in a temperature-controlled stage (LTS 350, Linkam Scientific). Images were captured with an 18 MP digital camera (OMAX) using the ToupView software package v. 3.7 (ToupTek Photonics).

Fractal Dimension—The fractal dimensions of the micrographs were determined through the box-counting method using Benoit v. 1.3 software (Trusoft International). Micrograph image contrast was increased before the determination of the box-counting fractal dimension. The fractal dimensions reported here were taken as an average from three micrographs. The fractal dimension indicates the homogeneity of mass distribution. For two-dimensional images, a fractal dimension of 2 represents a perfectly homogeneous mass distribution within that network, while a less evenly distributed (or clustered) mass has a lower fractal dimension.

Isothermal Crystallization—The crystallization behaviour of the samples at 5, 10, 15 and 20° C. was studied by measuring the SFC as a function of time using pulsed NMR (minispec mq20, Bruker). Samples in standard NMR tubes (height, 180 mm; diameter, 9 mm) were heated to 80° C. and held there for 30 min to destroy the crystal history. Next, they were placed in a water bath set at 5, 10, 15 and 20° C. and the SFC was subsequently measured at varying time intervals until equilibrium was reached.

Back Extrusion Mechanical Testing—Back extrusion testing was performed with a texture analyser (TA.HD.plus, Stable Micro Systems, Texture Technologies) equipped with a 30 kg load cell. Samples were transferred to glass test tubes (height, 125 mm; diameter, 14 mm) and stored for 1 week at their respective temperatures (5 or 22° C.) before testing. A cylindrical stainless-steel probe (height, 89 mm; diameter, 9.20 mm) with a truncated semispherical tip (height, 6.75 mm; diameter, 10.20 mm) penetrated the samples at a speed of 1.5 mm s−1 to a distance of 20 mm.

X-Ray Diffraction—X-ray diffraction spectra measurements were obtained using a Multiflex powder X-ray diffractometer (Rigaku MSC). Glycerolysis samples prepared under optimal glycerolysis conditions were melted and poured onto metal sample holders. Samples were then crystallized and stored at 5° C. for 1 week before measurements. A copper X-ray tube (Cu K$_{a1}$; λ=1.54 Å) was used as the X-ray source. Spectra were acquired at 25° C. in the 2θ 1.1°-35° diffraction angle region at a 0.5° min−1 acquisition speed with a divergence and scattering slit of 0.5°, and a 0.3 mm receiving slit.

Peanut Butter Formulation—Commercially available peanut flour (Bulk Barn Foods) was used as the base. Unaltered peanut oil (PO) (Walmart Canada) or peanut glycerolysis product (PGP) was melted at 50° C. and added to the flour, such that the fat content of the sample (46%) was similar to that of a traditional stabilized peanut butter.

Peanut Butter Stability—Peanut butter samples (5 g) were transferred to 50 ml centrifuge tubes and allowed to equilibrate for 24 h before testing. Samples were centrifuged for 40 min at 495 g at 22° C. This was the time required for oil separation in commercially available stabilized peanut butter. The separated oil was removed, and oil loss was calculated as a percentage.

Peanut Butter Texture Analysis—Commercially available stabilized peanut butter samples were tested in their original containers. Experimental peanut butter samples (30 g) were transferred to plastic containers and allowed to equilibrate for 24 h (settling of the sample within the containers ensured a level surface). A texture analyser (TA.HD.plus) equipped with a 30 kg load cell was used for texture measurements. Samples were penetrated to a distance of 5 mm, by a 1.1 cm diameter cylindrical stainless-steel probe with a rounded head, at a test speed of 0.5 mm s$^{-1}$. The probe was then retracted until free of the peanut butter sample. Three penetration tests were performed per container. All testing was performed at 22° C. Firmness of the peanut butter was taken as the force exerted at the maximum penetration depth.

Data Analysis—Three replicates (n=3) were performed for all experiments. All statistical analyses were carried out using GraphPad Prism v. 8.4.2 (GraphPad Software). Changes in the magnitude of dependent variables, in time or between treatments, were analysed using ordinary one-way analysis of variance, which uses an F-statistic criterion. Parametric statistics were used assuming Gaussian distribution of residuals, as the data passed all normality tests used ($\alpha$=0.05), including Anderson-Darling ($A^{*2}$), D'Agostino-Pearson omnibus ($K^2$), Shapiro-Wilk (W) and Kolmogorov-Smirnov (distance). Homoscedasticity was also tested using the Brown-Forsythe test, which uses an F-statistic criterion, and no significant differences in the standard deviations between samples were detected ($P>0.05$). In follow-up tests, the Tukey multiple-comparisons test (two-tailed) with hypothesis testing was used ($\alpha$=0.05), comparing the means of every data column with every other data column. For the data shown in FIG. 2.4$d$, an ordinary two-way analysis of variance was used. Significant differences between MAGs and glycerol ratios were detected (reported above), and data passed normality tests as described above for the ordinary one-way analysis of variance. Our data also passed the Spearman test for heteroscedasticiy, where the test explores if data cells with larger values have associated larger residuals; the data cells did not have larger residuals ($P>0.05$).

Results

Enzymatic glycerolysis was conducted with cottonseed oil, using *Candida antarctica* lipase B as the catalyst. Reactions were performed at 65° C. for between 6 and 72 h in the presence of a 2:1 (mol:mol) ratio of glycerol to TAG molecules. Additional reactions were performed at various glycerol:TAG molar ratios from 0.10:1 to 4:1 for 24 h. Glycerolysis reactions were performed under various conditions to optimize the structuring potential of the reaction.

MAG and DAG Content of Glycerolysis Reaction Products—FIG. 1$a$ depicts changes in MAG and DAG content as a function of reaction time for the lipase-mediated reaction between glycerol and cottonseed oil. The concentrations of MAGs and DAGs increased quickly in the early stages of the reaction, with MAGs increasing from less than 1% to over 20%, and DAGs increasing from 7% to 43% within 18 h. As the reaction proceeded, the rate of increase of MAGs remained high, increasing to 31.3% after 48 h, while DAG production had slowed down, rising to 49.1%. Further increases in reaction time to 72 h did not affect DAG composition (49.6%), while MAG content increased slightly to 34.3%.

The effect of glycerol content on MAG and DAG production is shown in FIG. 1$b$. Performing the reaction for 24 h at a 0.50:1 glycerol:TAG molar ratio resulted in a product containing 21.7% MAGs and 46.1% DAGs. Increasing the glycerol:TAG molar ratio to 1:1 increased the MAG content to 27.5%, without affecting the DAG content (45.3%). Further increases in glycerol content led to decreases in MAG and DAG concentrations. At a 4:1 glycerol:TAG molar ratio, MAG and DAG contents were reduced to 21.7% and 42.3%, respectively. The fatty acid composition for cottonseed oil is shown in Table 1. FIG. 1$c$/$d$ offer further insight into the contents of the major MAG molecular species produced. It should be noted that minor amounts of monostearin were also produced during the reaction. The monolinolein concentration remained relatively constant at longer reaction times and higher glycerol:TAG molar ratios. Moreover, monoolein and monopalmitin concentrations increased with reaction time, and also showed a clear maximum at a 1:1 glycerol:TAG molar ratio.

TABLE 1

| Fatty Acid | Cottonseed Oil | Peanut Oil |
| --- | --- | --- |
| 14:0 | 0.88 | — |
| 16:0 | 23.59 | 9.40 |
| 16:1 | 0.56 | — |
| 18:0 | 2.75 | 2.87 |
| 18:1 | 18.22 | 58.35 |
| 18:2 | 53.44 | 21.38 |
| 18:3 | 0.30 | — |
| 20:0 | — | 1.44 |
| 21:0 | — | 1.47 |
| 22:0 | 0.15 | 3.38 |
| 24:0 | 0.11 | 1.69 |

Figure 2:
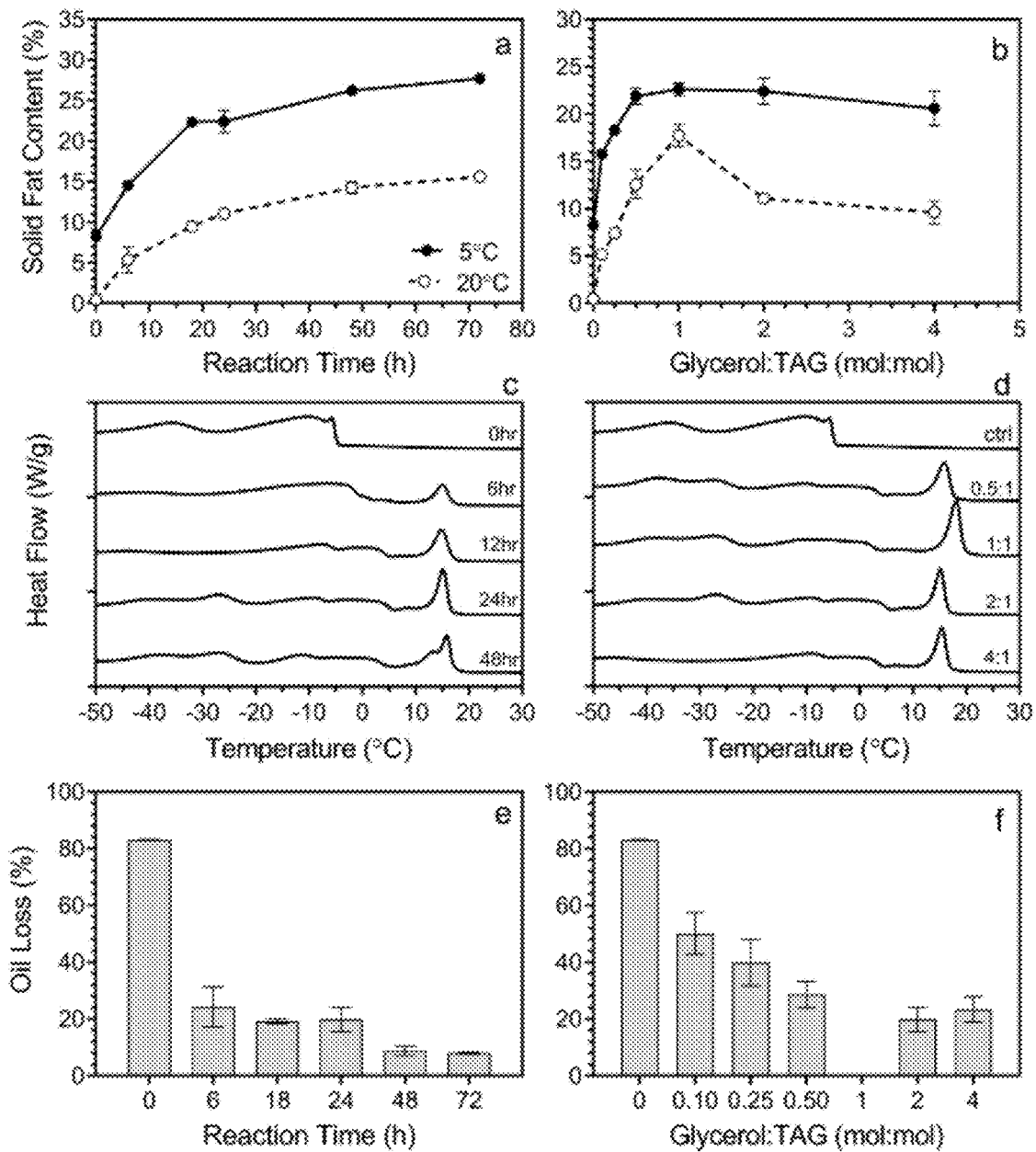
FIG. 2 graphically illustrates the effects of glycerolysis conditions on crystallization, SFC and oil binding, including: changes in SFC during glycerolysis of cottonseed oil at 5 and 20° C. as a function of reaction time at a 2:1 glycerol:TAG molar ratio (a) and at 24 h for different glycerol:TAG molar ratios (b) (values represent the means and standard deviations (error bars) of three replicates); differential scanning calorimetry crystallization thermograms for cottonseed oil before and after glycerolysis at various reaction times for a 2:1 glycerol:TAG molar ratio (c, top to bottom:oil control, 6 h, 18 h, 24 h, 48 h) and at different initial glycerol:TAG molar ratios after 24 h reaction time (d, top to bottom:oil control, 0.5:1, 1:1, 2:1, 4:1); oil loss (%) from cottonseed oil before and after glycerolysis for various reaction times (e) and at different glycerol:TAG molar ratios (f). Samples were stored at 5° C. for over 24 h before centrifugation at 16,110×g for 1 h at 5° C. Values represent the means and standard deviations (error bars) of three replicates.

Solid Fat Content—The extent to which the solid fat content (SFC) of cottonseed oil increased following glycerolysis was affected by both reaction time and glycerol concentration. Changes in SFC with respect to glycerolysis reaction time are shown in FIG. 2$a$. Native cottonseed oil contained 8.2% solids when equilibrated to 5° C. After 6 h, the SFC of the glycerolysis product was 14.6% at 5° C. After 18 h reaction time, the SFC increased to 22.4%, and remained constant until 24 h, increasing to 26.2% after 48 h. Further increases in the reaction time to 72 h lead to only minor increases in the SFC to 27.7%, indicating that the maximum structuring potential of the reaction had been reached after 48 h.

The relation between glycerol:TAG molar ratio and SFC, at both 5 and 20° C. is shown in FIG. 2$b$. Large changes in SFC ensued with increasing glycerol contents. Performing glycerolysis at the lowest glycerol:TAG molar ratio (0.10:1) yielded a sample that contained 15.8% solids at 5° C., an increase of over 7% from the native cottonseed oil. Using a glycerol:TAG molar ratio of 0.25:1 yielded a reaction product with an SFC of 18.3% at 5° C. When the ratio was increased to 0.50:1, the SFC rose to 21.9%. Increasing the glycerol content beyond this ratio had a limited effect on SFC at 5° C., causing only minor changes. The 1:1 glycerol:TAG molar ratio yielded a product with an SFC of 22.6% at 5° C., while the SFC produced using a 2:1 initial glycerol:TAG molar ratio was almost identical (22.4%). A slight decrease to 20.6% SFC was observed as the glycerol:TAG molar ratio was increased further to 4:1.

Figure 3:
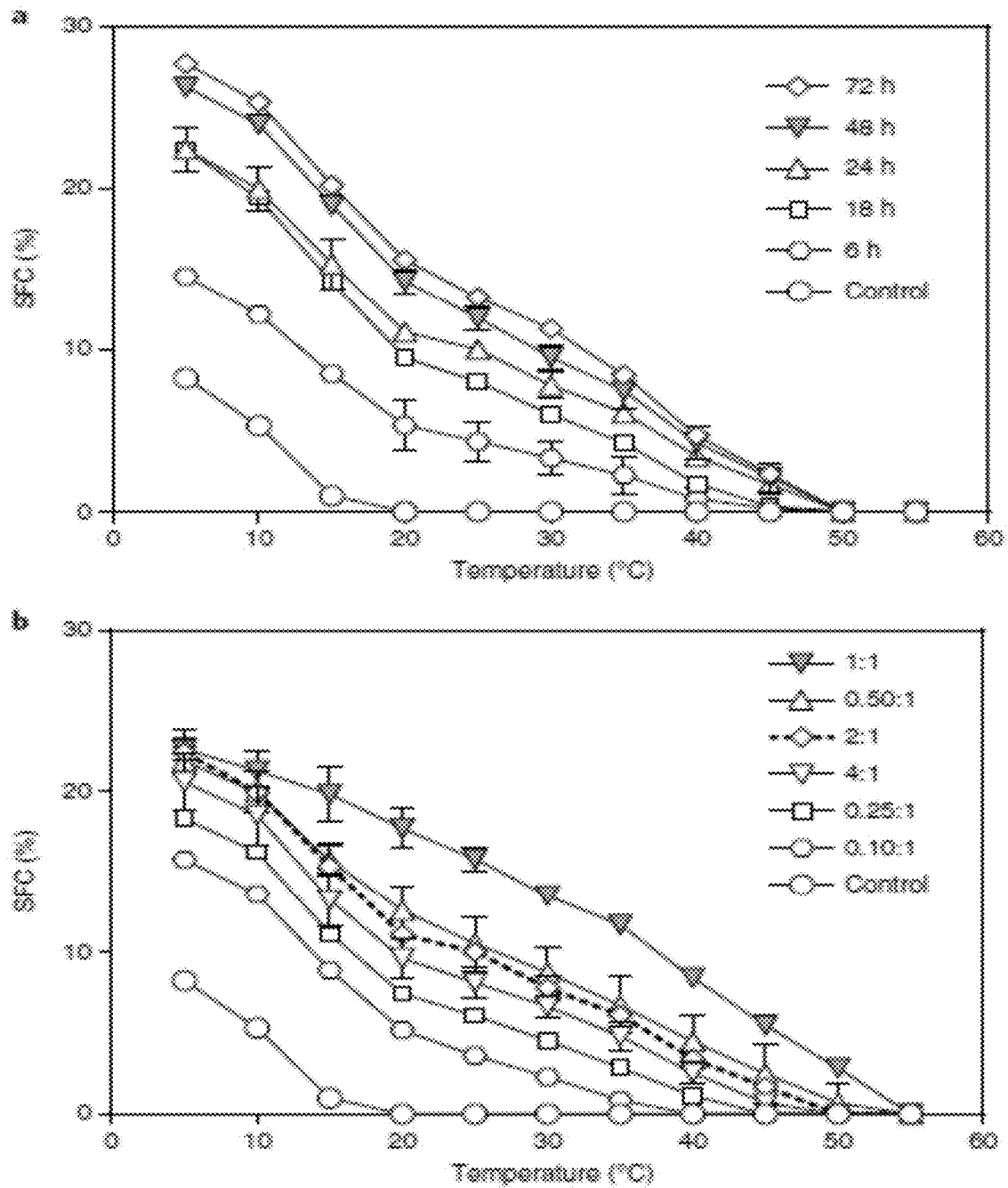
FIG. 3 graphically illustrates SFC melting profiles of glycerolysis reaction products including: SFC versus temperature melting profiles for cottonseed oil following glycerolysis at different reaction times (a), and at different glycerol:TAG molar ratios (b). Values represent the means and standard deviations (error bars) of three replicates.

The melting profiles (SFC as a function of temperature) of the cottonseed oil glycerolysis products at different reaction times (FIG. 3$a$) and for different glycerol:TAG molar ratios (FIG. 3$b$) indicate similar relative melting behaviour for all samples, with expected increases in the end-of-melt temperature and SFC as a function of increasing reaction time. The highest SFC and end-of-melt temperature was achieved at the 1:1 glycerol:TAG molar ratio at all temperatures, with even 0.5:1 and 2:1 molar ratios being lower.

Looking at the effects of reaction time, SFC clearly rises concomitantly with MAG/DAG concentrations (FIGS. 2a and 1a), reaching a plateau after 48 h. Since both MAG and DAG contents are increasing in a similar fashion, it is difficult to tell which of these components has a greater effect on SFC. This can be elucidated by comparing the SFC and MAG/DAG concentrations from the glycerol content experiments (FIGS. 2b and 1b). Changes in SFC as a function of time at 5° C. for different glycerol:TAG molar ratios are similar to changes in DAG concentration. On the other hand, changes in SFC as a function of time at 20° C. for different glycerol:TAG molar ratios more closely follow changes in MAG concentration, monoolein and monopalmitin specifically, each displaying maxima at the 1:1 glycerol: TAG molar ratio. This indicates that the amount of crystalline material is determined largely by MAGs at higher temperatures, as they constitute the primary structuring material at higher temperatures. At lower temperatures (5 and 10° C.), the DAGs had a greater effect on SFC. Moreover, it is interesting to note that the SFC-enhancing capabilities of MAGs and DAGs produced during glycerolysis were diminished when the original lipidic material already contained a high level of solids initially. Replacing high-melting TAGs with high-melting partial acylglycerols did lead to increases in SFC.

Differential Scanning calorimetry—Changes in SFC were well correlated to changes in crystallization and melting behaviour resulting from the MAGs and DAGs produced. This is depicted in the crystallization thermograms (FIG. 2c/d). Significant changes in crystallization behaviour were observed. Unreacted cottonseed oil had two crystallization regions with onsets at approximately −5° C. and −30° C. Following glycerolysis, a high-temperature crystallization peak appeared, with an onset of approximately 18° C. MAGs produced during the glycerolysis reaction are responsible for this peak since they are known to have a higher crystallization temperature than either DAGs or TAGs. Also, the onset of the crystallization peak initially located at −5° C. increased to approximately 5° C. This is consistent with DAG production. DAGs exist in two isomeric forms, 1,2-DAGs and 1,3-DAGs, and acyl migration results in 60-70% 1,3-DAGs within mixtures (Lo et al., 2008). 1,2-DAGs have a crystallization point similar to TAGs, while 1,3-DAGs crystallize approximately 10° C. higher than TAGs (Belitz et al, 2009; Lo et al., 2008). Moreover, as the reaction proceeded, the size of the high-temperature crystallization peak increased, corresponding to a greater MAG concentration (FIG. 2c).

FIG. 2d shows the effects of glycerol content on the crystallization behaviour of 24 h reaction products. The 1:1 glycerol:TAG molar ratio sample displays two distinctive features. First, the initial crystallization peak is noticeably larger, due to this reaction product having the highest MAG content. Second, and perhaps more importantly, this MAG crystallization peak is several degrees higher than that of the other samples. Since shifts in crystallization temperature result from differences in molecular species present, this must be due to the higher content of monopalmitin produced with a 1:1 glycerol:TAG molar ratio.

Oil-Binding Capacity—Glycerolysis proved to be an effective method of improving the oil-binding capacity (OBC) of the system. The relation between oil loss and reaction time is shown in FIG. 2e. Native cottonseed oil displayed an oil loss of ~83% under the test conditions (centrifugation: 1 h, 16,110 g, 5° C.). Enzymatic glycerolysis for 6 h resulted in a product with an oil loss of ~24%. This was reduced to less than 20% when the reaction was carried out for 18 h. Increasing the reaction time from 18 to 24 h did not affect OBC, which is not surprising since there were only minimal changes in SFC and MAG/DAG contents during this time. After 48 h, oil loss decreased to less than 9%. OBC was only slightly improved by increasing the reaction time to 72 h. Furthermore, large differences in OBC were observed when the glycerolysis reaction was performed with different glycerol:TAG molar ratios, as depicted in FIG. 2f. There is a clear oil loss minimum at the 1:1 glycerol:TAG molar ratio, where no oil loss was observed. Glycerolysis reaction time results indicate that OBC was strongly dependent on SFC, and in turn, on MAG and DAG concentrations. Moreover, differences in OBC for different glycerol:TAG molar ratios cannot be explained by the 5° C. SFC data, nor can they be explained by the DAG contents, as 0.50:1, 1:1 and 2:1 glycerol:TAG molar ratio samples each contained similar levels of both solids and DAGs. This indicates that MAG concentration (monopalmitin and monoolein in particular) had the greatest effect on OBC.

Microstructure—Microstructural differences between these three reaction products shed more light on the OBC results. The 1:1 glycerol:TAG molar ratio sample (FIG. 4b) contained numerous smaller crystals, while both the 0.5:1 (FIG. 4a) and 2:1 (FIG. 4c) glycerol:TAG molar ratio samples contained fewer crystals, most of which were larger than those of the 1:1 ratio sample. Furthermore, corresponding fractal dimension values, which characterize the spatial distribution of crystalline mass in the networks, were determined from the micrographs. The fat crystal network of the 1:1 glycerol:TAG molar ratio reaction product had a box-counting fractal dimension, and corresponding standard deviation, of 1.77±0.01. This was significantly greater (P<0.0001) than the fractal dimensions observed for the 0.5:1 (1.54±0.03) and 2:1 (1.57±0.03) ratios. The fractal dimension values for the 0.5:1 and 2:1 glycerol:TAG molar ratio sample networks were quite similar, similar to trends in oil loss from these two reaction products. These findings demonstrate that the increased homogeneity in spatial distribution of crystalline mass for the 1:1 glycerol:TAG molar ratio reaction product resulted in a greater binding of the liquid oil within the crystalline network.

Figure 4:
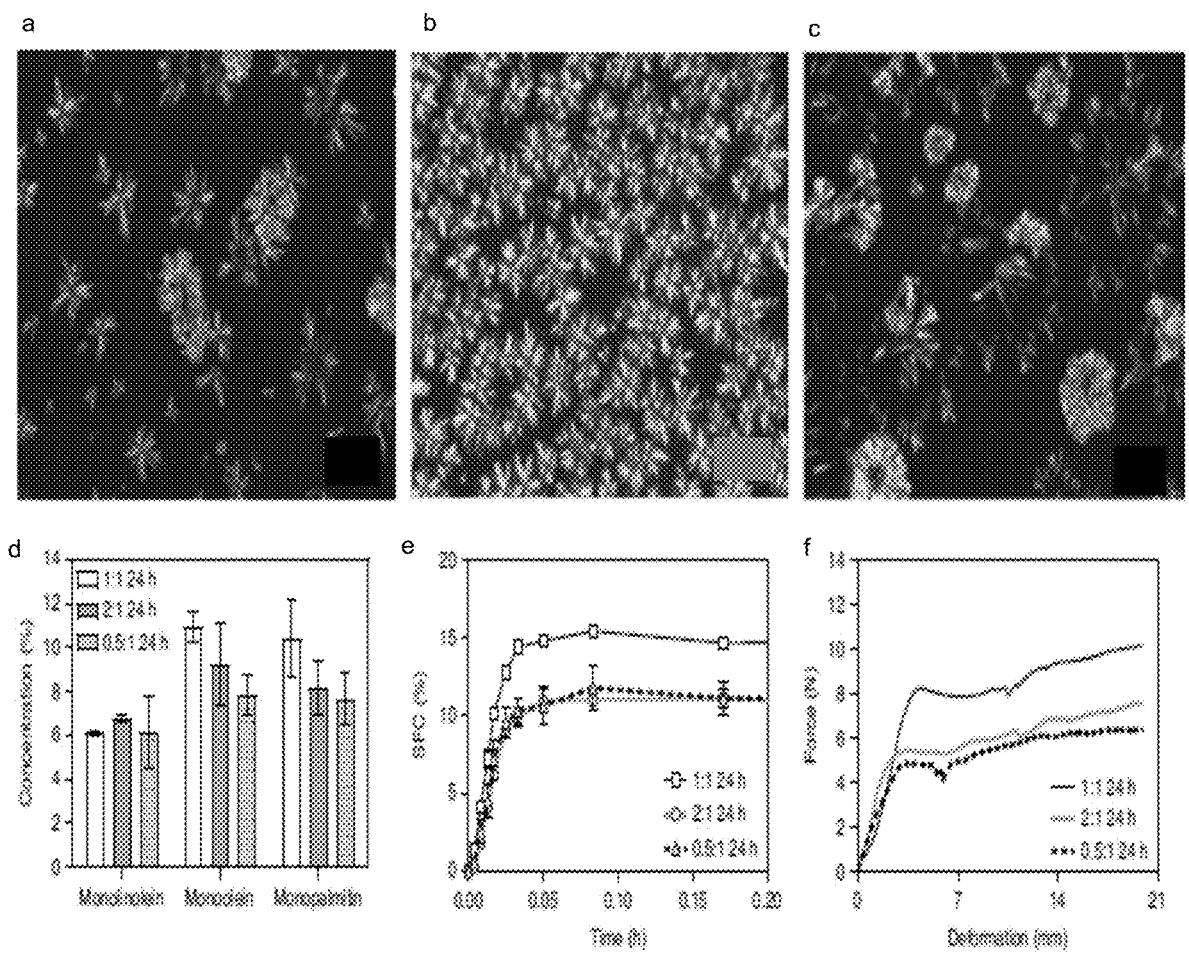
FIG. 4 illustrates micrographs of glycerolysis products after 24 h reaction time for glycerol:TAG molar ratios of 0.5:1 (a), 1:1 (b) and 2:1 (c), and graphically illustrates (d) individual MAG molecular species content, (e) SFC-time profiles during isothermal crystallization at 15° C., and (f) back extrusion force-deformation profiles for the glycerolysis products of reactions performed for 24 h, at 0.5:1, 1:1 and 2:1 glycerol:TAG molar ratios. Values represent the means and standard deviations (error bars) of three replicates.

The unique microstructure of the 1:1 glycerol:TAG molar ratio sample is due to the MAG composition. For comparative purposes, individual MAG contents are shown again in FIG. 4d. Statistical analysis demonstrated a significant effect of glycerol:TAG molar ratio on both MAG molecular species (P=0.007) and total MAG contents (P=0.032). Compositional differences resulted in an earlier onset of crystallization, as mentioned earlier, which translated into greater increases in SFC during the initial stages of crystallization. The isothermal crystallization curves of the three systems at 15° C. are shown in FIG. 4e. For all temperatures tested, the 1:1 glycerol:TAG molar ratio displayed the fastest isothermal crystallization kinetics with the smallest half-time of crystallization ($t_{1/2}$). These differences in crystallization behaviour led to the formation of a crystal network containing smaller, more numerous fat crystals, with a higher fractal dimension. As a result of the smaller crystals and more homogeneous crystal network, the 1:1 glycerol:TAG molar ratio reaction product was firmer than either the 0.5:1 or 2:1 ratio product, as measured by back extrusion (FIG. 4f).

Figure 5:
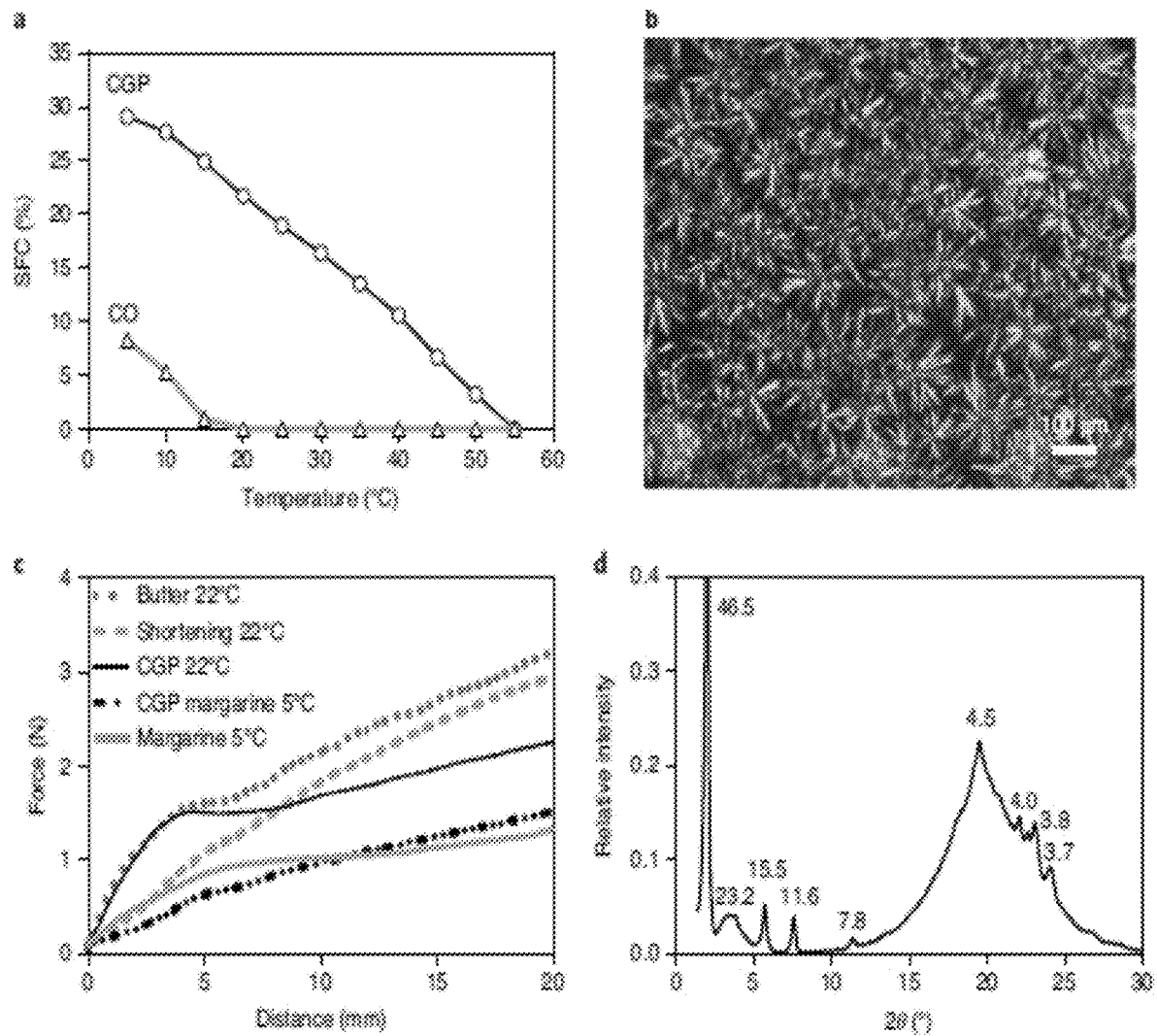
FIG. 5 illustrates (a) SFC melting profiles for cottonseed oil (CO) and the cottonseed oil glycerolysis product (CGP) (reaction time, 48 h; glycerol:TAG molar ratio, 1:1). Values represent the means and standard deviations of three replicates. Error bars are smaller than the data points; (b) Micrograph of CGP; (c) Back extrusion force-deformation profiles for commercially available tub margarine, butter and shortening as well as for CGP and for margarine prepared using CGP. Values represent the means of three replicates; and (d) Powder X-ray diffraction spectra for the CGP.

In these sets of experiments, the 1:1 glycerol:TAG molar ratio reaction product displayed a very high OBC and unique melting properties, which extends the functional range of the product. Performing glycerolysis at this glycerol:TAG molar ratio for 48 h increased the fractal dimension to 1.85 while maintaining the unique crystal morphology (FIG. 5b). This cottonseed glycerolysis product, because of its high fractal dimension, displayed no oil loss. FIG. 5a displays the SFC-temperature melting profile of this product. At 5° C., the glycerolysis product had an SFC of 29.1% and retained a high level of crystalline material as the temperature was increased, with 21.7% solids remaining at 20° C. The X-ray diffraction spectra obtained for this cottonseed glycerolysis product (FIG. 5d) showed a large peak in the short-spacing (wide-angle) region at 4.55 Å, along with several smaller peaks. This peak position is characteristic of MAG crystals in the β polymorphic form. The (001) peak in the long-spacing (small-angle) region at 46.48 Å indicated that the crystals were primarily composed of monopalmitin, which in its pure neat form displays a peak at 45.8 Å.

Furthermore, increases in crystallization temperature and SFC of the cottonseed oil resulting from glycerolysis demonstrate the potential of this process for producing a substitute for palm oil and/or interesterified blends of hydrogenated oils, with improved sustainability and health properties. When used to produce margarine, the cottonseed glycerolysis product demonstrated flow behaviour and hardness similar to that of commercially available soft-tub margarine (FIG. 5c). Additionally, the cottonseed glycerolysis product demonstrated plastic flow behaviour when back extrusion was performed, and even showed yielding properties similar to those of butter when tested at 22° C. (FIG. 5c).

Figure 6:
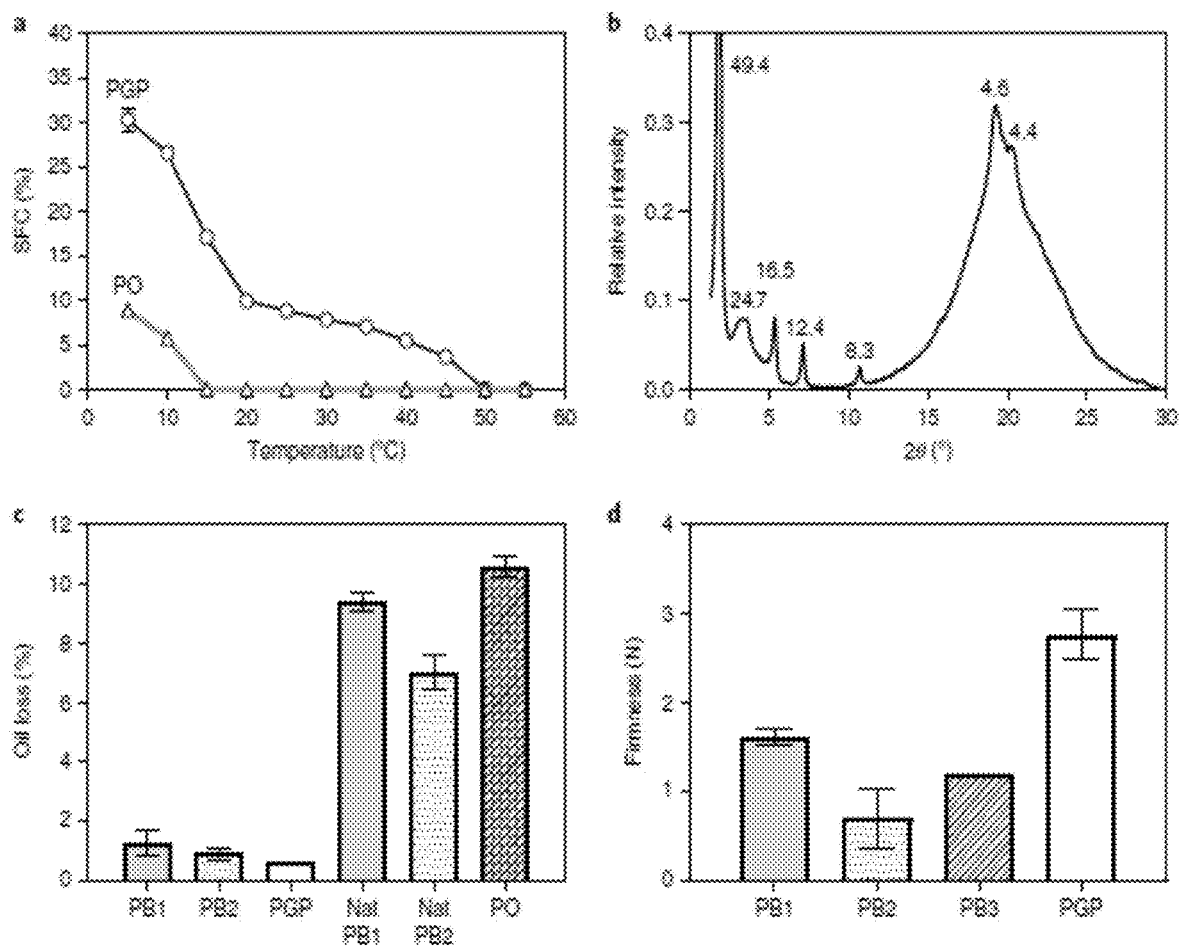
FIG. 6: Stabilization of peanut butter with peanut oil glycerolysis product. (a) SFC melting profiles for peanut oil (PO) and the peanut oil glycerolysis product (PGP) (reaction time, 48 h; glycerol:TAG molar ratio, 1:1). Values represent the means and standard deviations of three replicates. Error bars are smaller than the data points. Inset: experimental peanut butter samples prepared by mixing peanut flour with PO and PGP. (b) X-ray diffraction spectrum of the PGP. (c,d) Properties of experimental and commercial brand peanut butters: oil loss (c) and firmness (d). PB1 and PB2, stabilized commercial brand peanut butters; Nat PB1 and Nat PB2, natural unstabilized commercial brand peanut butters. Note that the natural unstabilized and PO experimental peanut butters were too weak to measure a firmness value. Values represent the means and standard deviations (error bars) of three replicates.

This structuring technology would also be of great benefit in stabilizing peanut butter. Peanut oil underwent significant changes following glycerolysis. The SFC of peanut oil increased from 9% to 30% when measured at 5° C., and 10% solids remained at 20° C. (FIG. 6a), while X-ray diffraction patterns were characteristic of MAGs in the β polymorphic form (FIG. 6b). The stabilizing ability of this peanut oil glycerolysis product is shown in FIG. 6c and FIG. 6a inset, reducing the level of oil separation following centrifugation to that of commercially available stabilized products. Moreover, the firmness of peanut butter prepared with the peanut glycerolysis product in our work, and no stabilizers, was slightly higher than that of commercial smooth peanut butter containing stabilizers (FIG. 6d), but this could easily be adjusted by blending with unmodified liquid oil if required.

Discussion

Structuring peanut oil using glycerolysis may well be a favourable alternative as it does not change the fatty acid composition, while reducing saturated fat content. Margarine and shortening produced from glycerolysis-structured oils of assorted varieties could help reduce demand for palm oil, curbing the environmental destruction taking place throughout the world's rainforests. Using glycerolysis-structured oils in these food materials would also decrease the need for hydrogenated vegetable oils. Reducing the usage of palm oil and hydrogenated oils in favour of glycerolysis-structured oils will increase MUFA and PUFA consumption while decreasing SFA intake, with beneficial effects on serum cholesterol levels and cardiovascular risk. Glycerolysis-structured oils also carry numerous health benefits associated with consuming DAGs in place of TAGs. While MAGs are a common food ingredient, they are typically consumed in low quantities, and therefore clinical trials would be recommended to ensure the safety of these glycerolysis-structured oils prior to bringing them to market.

Implementing enzymatic glycerolysis on an industrial scale, as a batch or continuous process, would be straightforward given that enzymatic inter-esterification is already in use. Enzymatic interesterification is a process commonly used in the food industry to interesterify hydrogenated oils with liquid vegetable oils and requires the same equipment that would be necessary for enzymatic glycerolysis. The only additional cost would be for glycerol, which is an inexpensive, readily available material.

Example 2—Conversion of a Variety of Edible Oils into Structural Fats Via Glycerolysis Glycerolysis was applied to additional oils, including Tigernut oil, olive oil, soybean oil, canola oil, rice bran oil and algal oil, as described in Example 1 to convert the oils into a structured fat product.

Methods and Materials

Materials—Tigernut oil was generously provided by a local producer (The Chufa Co.; Toronto, ON, Canada). Cottonseed oil was purchased online (Bass Pro Shops; Springfield, Mo., USA). Peanut, olive, soybean, canola oils were purchased from a local supermarket (Wal-mart Canada Corp.). Rice bran oil was purchased from New Directions Aromatics (New Directions Inc.; Mississauga, ON, Canada). High-oleic canola oil (HOCO) was obtained through a supplier (Bunge Limited; Chesterfield, Mo., USA). Sesame oil was provided by Soybean Crushing Co. & Derivatives (SOYA; Saudi Arabia). High-oleic algal oil (HOAO) was a gift from Solazyme Inc. (San Francisco, Calif., USA). Glycerol (99.9% Glycerol, Fisher Scientific; Ottawa, ON, Canada) was obtained through a scientific material supplier. *Candida antarctica* lipase B immobilized on Immobead 150 was purchased from Sigma-Aldrich (Sigma-Aldrich; St. Louis, Mo., USA).

Fatty Acid Composition—Fatty acid composition for each of the oils was determined as described in Example 1.

Glycerolysis Reaction—Glycerol was added to oil (30 g) at a glycerol to triacylglycerol molar ratio of 1:1, and the glycerolysis reaction was conducted as described in Example 1 for 48 hours. MAG and DAG contents were determined also as previously described.

X-Ray Diffraction—X-ray diffraction spectra measurements were performed as previously described.

Margarine Preparation—Margarine samples were prepared in 100 g batches from tigernut oil following glycerolysis performed under optimal reaction conditions. The oil phase represented 81 wt % of the margarine. Sodium chloride (1.8 wt %) and 0.1 wt % potassium sorbate (Sigma-Aldrich) were dispersed in water (17.1 wt %). The water phase was added to the oil phase and mixed with an immersion blender until completely homogenous. Samples were then spread on a stainless-steel tempering table maintained at 5° C. and sheared for several minutes with a plastic bench scraper in order to induce crystallization. Margarine samples were then stored at 5° C. for 1 week.

Solid Fat Content Melting Profile—SFC was measured as previously described.

Differential Scanning calorimetry—Differential scanning calorimetry was conducted as previously described. Margarine samples prepared with the tigernut oil reacted under optimal glycerolysis reaction conditions, which had previously been crystallized and stored at 5° C. for 1 week, were equilibrated at 5° C. for 2 h before being heated to 50° C. A commercially, available soft-tub margarine was also tested in the same fashion. In all cases, 8-10 mg of sample was placed in aluminum crucibles that were hermetically sealed prior to testing.

Polarized Light Microscopy—Microstructure was characterized by polarized light microscopy as previously described. Furthermore, the stored experimental margarine sample was transferred to the microscope slide and imaging was performed immediately.

Margarine Back Extrusion—Back extrusion was performed as previously described. Prior to testing, margarine samples were transferred to glass test tubes (h: 125 mm; d: 14 mm) and stored for 1 week at 5° C.

Data Analysis—Three replicates (n=3) were performed for all experiments. Data was analyzed using GraphPad Prism 5.0 (GraphPad Software, Inc., La Jolla, Calif., USA). A one-way analysis of variance (ANOVA) was performed along with a Tukey's multiple comparison test to determine differences between treatments. Treatments were taken as significantly different when P<0.05.

Results and Discussion

Acylglycerol Composition—Optimal glycerolysis reaction conditions were determined to be 48 h with a 1:1 glycerol:TAG molar ratio when 2 w/w % enzyme was used as the catalyst in cottonseed oil as described in Example 1. Following glycerolysis under these conditions, the cottonseed system contained 34.8% monoacylglycerols (MAGs), 49.6% diacylglycerols (DAGs), and 17.1% triacylglycerols (TAGs). To characterize the production of partial acylglycerols, glycerolysis was performed under optimized reaction conditions with tigernut, peanut, rice bran, and soybean oils. Subsequently, the MAG, DAG, and TAG concentrations were determined. After glycerolysis, the tigernut system contained 31.2% MAGs, 42.3% DAGs, and 26.5% TAGs. The peanut glycerolysis product was composed of 31.6% MAGs, 46.8% DAGs, and 21.6% TAGs. The rice bran system contained 31.4% MAGs, 47.8% DAGs, and 20.8% TAGs, and the soybean glycerolysis product contained 33.2% MAGs, 44.8% DAGs, and 22.0% TAGs. It is noted that although free fatty acids (FFA) were not quantified for each of the oil systems examined, they were measured in the peanut oil system. The FFA content was approximately 0.3% in the native oil and remained below 2% following the glycerolysis reaction. A peak for the FFAs was not observed during the HPLC analysis of the MAG, DAG, and TAG concentrations. Given the presence of a small amount of FFA, it is recognized that the total MAG, DAG and TAG portion of the glycerolysis reaction products is representative of the remainder of the total material (>98%). These results demonstrate that when glycerolysis is performed under defined conditions, similar acylglycerol levels will be produced regardless of the reacted oil. Therefore, it expected that any vegetable oil, when reacted with 2% w/w *Candida antarctica* lipase B in the presence of a 1:1 glycerol:TAG molar ratio for 48 h, will contain upwards of 30% MAGs, 40-50% DAGs, with as low as 20% TAGs remaining. For this reason, glycerolysis was performed under these conditions on several additional vegetable oils to further study the physical properties of the glycerolysis reaction products, without quantification of partial acylglycerols. Furthermore, the fatty acid composition was determined for each of the unaltered oils. Results are shown in Table 2.

TABLE 2

Average fatty acid compositions for each of the unaltered oils used in this study.

| Fatty Acid | Tigernut | Peanut | Cottonseed | Rice Bran | Olive | HOCO | Soybean | Sesame | Canola | HOAO |
|---|---|---|---|---|---|---|---|---|---|---|
| 14:0 | — | — | 0.88 ± 0.00 | 0.32 ± 0.02 | — | — | — | — | — | 0.41 ± 0.00 |
| 16:0 | 13.47 ± 0.03 | 9.40 ± 0.01 | 23.59 ± 0.04 | 18.76 ± 0.01 | 11.49 ± 0.01 | 3.86 ± 0.01 | 10.61 ± 0.01 | 10.00 ± 0.02 | 4.14 ± 0.01 | 1.64 ± 0.01 |
| 16:1 | — | — | 0.56 ± 0.01 | 0.22 ± 0.01 | 0.83 ± 0.01 | — | — | — | — | — |
| 18:0 | 6.60 ± 0.02 | 2.87 ± 0.01 | 2.75 ± 0.01 | 2.09 ± 0.01 | 2.65 ± 0.01 | 1.75 ± 0.01 | 4.67 ± 0.02 | 5.94 ± 0.01 | 1.82 ± 0.01 | 0.71 ± 0.00 |
| 18:1 | 68.14 ± 0.03 | 58.35 ± 0.01 | 18.22 ± 0.02 | 41.61 ± 0.03 | 75.07 ± 0.02 | 72.54 ± 0.03 | 21.63 ± 0.04 | 39.72 ± 0.01 | 63.13 ± 0.04 | 92.01 ± 0.04 |
| 18:2 | 10.30 ± 0.01 | 21.38 ± 0.01 | 53.44 ± 0.03 | 33.95 ± 0.05 | 8.99 ± 0.01 | 16.58 ± 0.02 | 54.40 ± 0.06 | 43.69 ± 0.01 | 20.00 ± 0.03 | 4.28 ± 0.01 |
| 18:3 | 0.78 ± 0.00 | — | 0.30 ± 0.00 | 0.90 ± 0.01 | 0.97 ± 0.01 | 3.70 ± 0.02 | 8.12 ± 0.01 | 0.66 ± 0.00 | 9.74 ± 0.01 | 0.95 ± 0.01 |
| 20:0 | 0.13 ± 0.01 | 1.44 ± 0.01 | — | 0.76 ± 0.03 | — | — | 0.22 ± 0.01 | — | — | — |
| 21:0 | 0.17 ± 0.01 | 1.47 ± 0.01 | — | 0.56 ± 0.01 | — | 1.26 ± 0.01 | 0.35 ± 0.01 | — | 1.17 ± 0.01 | — |
| 22:0 | 0.14 ± 0.01 | 3.38 ± 0.01 | 0.15 ± 0.01 | 0.31 ± 0.00 | — | — | — | — | — | — |
| 22:1 | — | — | — | — | — | 0.31 ± 0.01 | — | — | — | — |
| 24:0 | 0.27 ± 0.00 | 1.69 ± 0.01 | 0.11 ± 0.01 | 0.50 ± 0.02 | — | — | — | — | — | — |

Values indicate the mean and standard deviation of three replicates and are represented as a mass percentage (% w/w).

Figure 7:
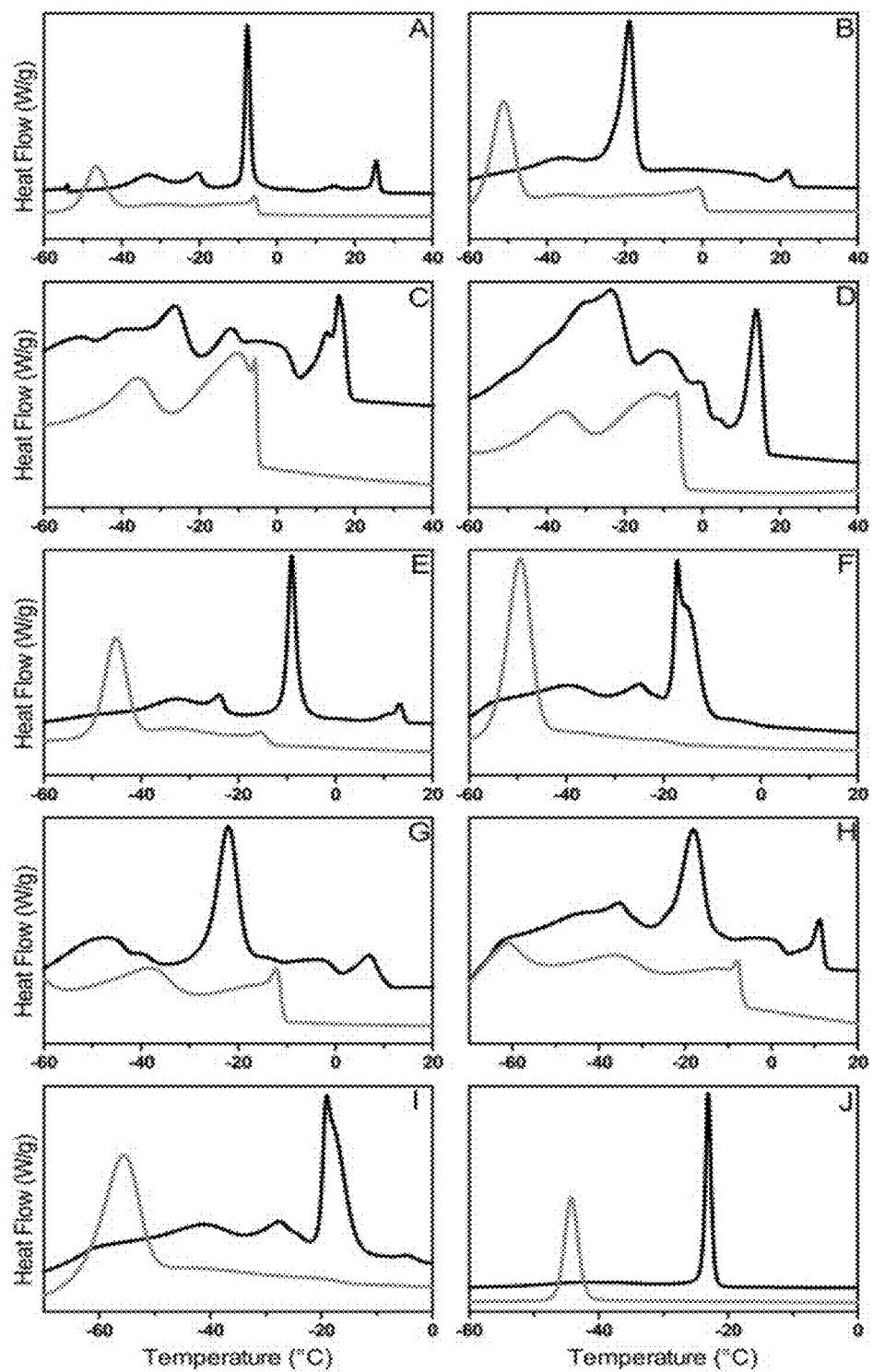
FIG. 7 illustrates the differential scanning calorimetry crystallization profiles for glycerolysis reaction products (black lines) and their respective oils (gray lines) including: (A) tigernut; (B) peanut; (C) cottonseed; (D) rice bran; (E) olive (F) high oleic canola oil (HOCO); (G) soybean; (H) sesame; (I) canola; and (J) high oleic algal oil (HOAO).

Physical Properties—The production of MAGs and DAGs through glycerolysis altered the crystallization and melting behaviour of each of the oils, as measured by differential scanning calorimetry (DSC). Crystallization curves for each of the vegetable oils, before and after the optimized glycerolysis reaction, are shown in FIG. 7. For each oil tested, a different crystallization profile was obtained following glycerolysis. In all cases, the presence of new molecular species produced a crystallization peak with a crystallization onset that was approximately 20° C. higher than that displayed for the unaltered oil systems. For glycerolysis systems containing greater than 10% saturated fatty acids (SFAs) this was observed as a new high temperature crystallization peak separate from the bulk of the material. Tigernut (FIG. 7A), peanut (FIG. 7B), cottonseed (FIG. 7C), rice bran (FIG. 7D), olive (FIG. 7E), soybean (FIG. 7G), and sesame (FIG. 7H) fall into this category. For lipid systems containing low levels of SFAs (i.e., HOCO (FIG. 7F), canola (FIG. 7I), and HOAO (FIG. 7J)), there was a shift in the bulk crystallization.

Several additional points and similarities were noted. First, the highest crystallization onset temperature was observed with the tigernut glycerolysis product, and tigernut and peanut glycerolysis products were the only systems that displayed high temperature crystallization peaks above 20° C. The profile for the olive glycerolysis product resembled that of the tigernut glycerolysis product, however the high temperature peak was shifted to a lower temperature, likely the result of a lower SFA content (14.1% vs 20.8%), but otherwise had similar fatty acid profiles. Furthermore, the high temperature crystallization peaks observed for the cottonseed and rice bran glycerolysis products were proportionally very large compared to each of the other systems. This was potentially due to their SFA contents (27.5% and 23.3%, respectively), which happen to be the highest of the oils studied. Striking similarities between the crystallization behaviour of HOCO and canola glycerolysis systems were evident, however, crystallization onset in the HOCO system began at a slightly elevated temperature. This likely would have been due to the higher oleic acid content of HOCO (72.5% vs 63.1%), given that the SFA contents are practically identical. Finally, HOAO, which is composed mostly of triolein, had a single, sharp crystallization peak below −40° C. Following production of MAGs and DAGs through glycerolysis, this peak was shifted to a higher temperature by around 20° C. It should be noted that since no high temperature crystallization peaks were obtained, no solids were present in the HOAO glycerolysis product when stored at 5° C. Consequently, x-ray diffraction (XRD) spectra and micrographs could not be obtained for the HOAO system.

Figure 8:
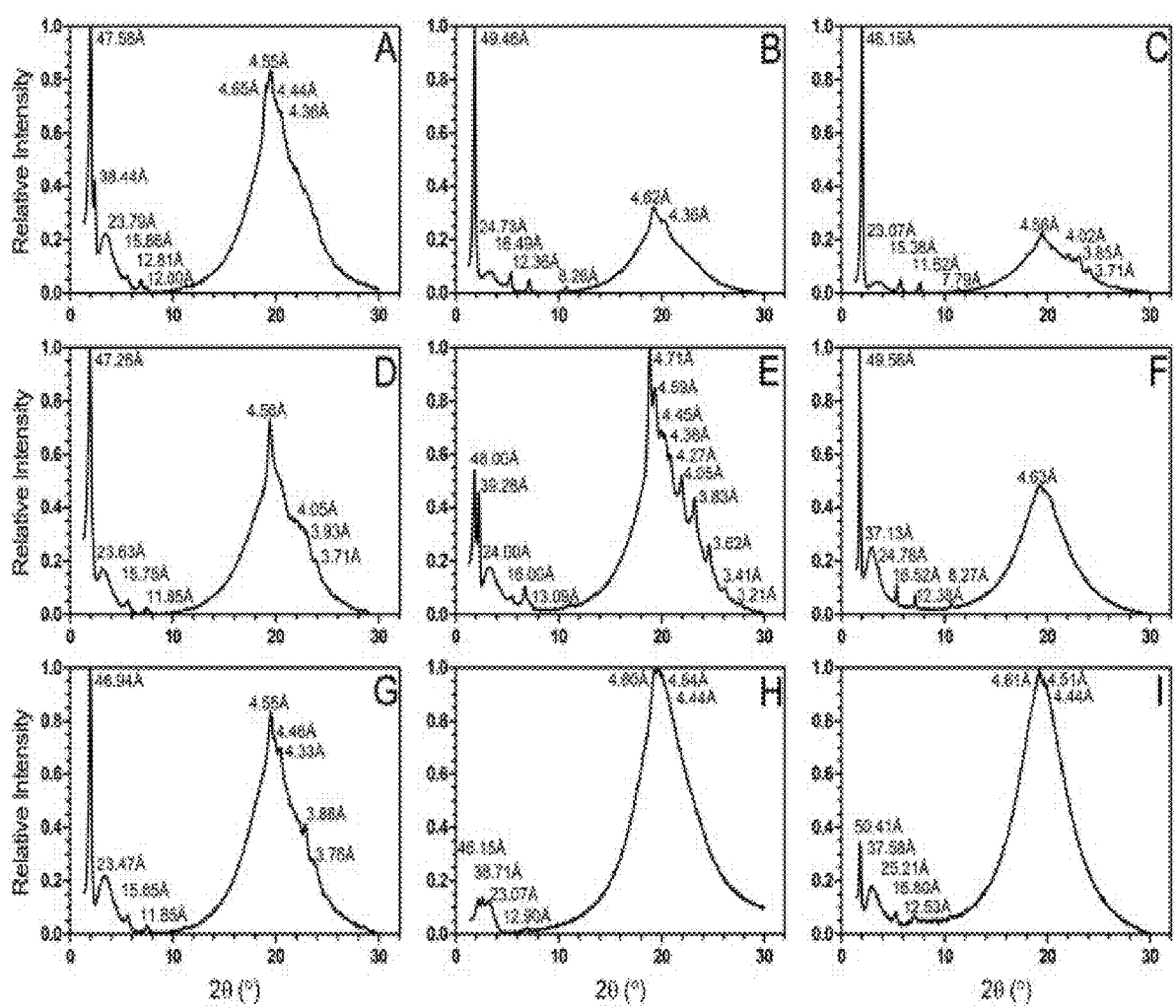
FIG. 8 illustrates X-Ray diffraction spectra obtained for glycerolysis reaction products of (A) tigernut oil; (B) peanut oil; (C) cottonseed oil; (D) rice bran oil; (E) olive oil (F) high oleic canola oil (HOCO); (G) soybean oil; (H) sesame oil; (I) canola oil. Measurements were performed after crystallization and storage at 5° C. for 1 week.

X-Ray Diffraction—XRD spectra for the optimized glycerolysis products, crystallized statically and stored for a minimum of 1 week at refrigeration temperatures, are shown in FIG. 8. Peanut and HOCO glycerolysis products displayed short-spacings peaks just above 4.6 Å (4.62 and 4.63 Å, respectively), while each of the other systems, displayed short-spacings peaks between 4.5 and 4.6 Å. This demonstrates the presence of MAG crystals in the β polymorphic form. In each system, except the olive glycerolysis product, this peak dominated the wide-angle region, indicating that the β-form MAG crystals were the primary structuring material. For the olive system, the peak of greatest intensity was located at 4.71 Å. This peak, along with the peak at 3.83 Å correspond with the short-spacings of 1,3-diolein crystals. Therefore, diolein crystals were the primary structuring material of the olive glycerolysis product, while MAG crystals acted as secondary crystals in the structural matrix.

The diffraction peak corresponding to the (001) crystal plane in the long-spacing region (small-angle) was positioned at between 46 and 50 Å for each of the systems. Higher order reflections, namely (002), (003) and (004), were also evident in the spectra, and are characteristic of lamellar phases, with relative positions at 1:1/2:1/3:1/4 in real space or 1:2:3:4 in inverse space ($q=2\pi c/d$). The position of the 001 peak for each of the systems is dependent on the composition of the MAGs making up the crystals. In their pure forms, monopalmitin and monostearin β crystals are known to display peaks at 45.8 Å and 50.0 Å, respectively. Additionally, pure β crystals of monoolein have been observed with a peak at 49.52 Å. The presence of MAGs containing long-chain saturated fatty acids (i.e., 20:0, 21:0, 22:0, 24:0) would also influence the position of the 001 diffraction peak. Finally, although monolinolein (and sometimes monolinolenin) would be present in substantial quantities in many of the systems, these MAG species have crystallization temperatures well below the crystallization and storage temperature that these samples were subjected to and as a result, are unlikely to have been incorporated into the crystal network. Furthermore, 1,3-diolein crystals are known to have a long-spacing of 39.3 Å. A peak in this region was present in the tigernut, olive, HOCO, sesame, and canola systems following glycerolysis, indicating that 1,3-diolein co-crystallized with the MAGs. However, it was only within the olive system that diolein was the dominant crystal within the network, as was determined from the wide-angle region. In all other systems, the diolein crystals were secondary to the MAG crystals.

The MAG crystal peak position for the cottonseed glycerolysis product (46.15 Å) corresponds with crystals composed almost entirely of monopalmitin. This stands to reason, as cottonseed oil contained approximately 23.6% palmitic acid with less than 3% stearic acid and has the lowest oleic acid content (18.2%) of any of the oils. The sesame glycerolysis product also had a long-spacing of 46.15 Å, again indicating MAG crystals composed mainly of monopalmitin. However, the amplitude of this peak was extremely low, demonstrating that there was very little MAG crystal matter present in the system. Furthermore, MAG peaks for soybean and rice bran systems were located at 46.94 and 47.26 Å, respectively. These long-spacings again indicate that monopalmitin is the major MAG species incorporated into these crystals. Since the oleic acid concentration (21.6%) for soybean oil was low, the increase in the long-spacing was likely due to the incorporation of stearic acid within the MAG crystals. For the rice bran system, the higher oleic acid concentration (41.6%) would have played an important role. The long-spacing increased further to 47.58 Å for the tigernut glycerolysis product. While this value remains closer to that of monopalmitin than to monoolein or monostearin, increased concentrations of both oleic acid (68.1%) and stearic acid (6.6%) contributed to the observed increase. The long-spacing of the olive glycerolysis product was 48.00 Å. This MAG crystal value is now closer to that of monoolein than to monopalmitin, meaning that a lower proportion of monopalmitin was present in the crystal structure compared to the combination of monoolein and monostearin. The peanut glycerolysis product MAG crystals had a long-spacing of 49.46 Å. Peanut oil had an interesting fatty acid composition, with SFAs containing ≥20 carbons making up 8.0%. This combined with the stearic acid content (2.9%) was greater than the palmitic acid content (9.4%). Additionally, peanut oil contained a high amount of oleic acid (58.4%) and given that pure monoolein crystals have an almost identical long-spacing to this system, monoolein likely contributed substantially. The HOCO glycerolysis product had a very similar long-spacing (49.56 Å). A major contribution from the high oleic acid content (72.5%) and only minor contributions from SFAs (6.9%) resulted in a long-spacing very close to that of pure monoolein. Similarly, canola had a low SFA content (7.1%), meaning that monoolein contributed substantially to the MAG crystals (50.41 Å).

Microstructure—The similarities between the crystal morphology of the cottonseed, rice bran, and soybean glycerolysis products was noticeable. Each containing needle-like crystals of 50-100 μm diameter. In contrast, the tigernut oil glycerolysis product formed a crystal network composed of smaller platelet-like crystals (20-50 μm) which aggregated to form larger crystal structures. The crystals of the olive glycerolysis product had a similar morphology, containing aggregates of platelet-like crystals. However, the platelets within the olive system were larger for the most part, while the aggregated structures were smaller. Furthermore, the peanut glycerolysis product contained platelet-like crystals of a similar size to those within the tigernut system, but they had arranged themselves in a different manner. Within the sesame glycerolysis product, again were platelet-like crystals, but these crystals were large (20-70 μm diameter), round, and tightly packed in small clusters of several crystals. Finally, the crystalline material within both the HOCO and canola glycerolysis products formed extensive structures, of similar morphologies, within the oil phase. It is important to note that in the bulk sample, stored at 5° C., the liquid and crystalline materials formed two distinct phases in both the HOCO and canola systems, while each of the other glycerolysis products showed no phase separation.

The fatty acid composition along with the crystallization behaviour and XRD spectra help to explain some of the similarities and differences among the microstructures of the oil systems. To begin with, the extensive structures extending throughout the liquid phase were unique to the HOCO and canola systems. Also unique to the HOCO and canola systems was that the starting oils contained less than 10% SFAs (6.9% and 7.1%, respectively) and greater than 60% oleic acid (72.5% and 63.1%, respectively). This produced MAG crystals, with long-spacings close to that of neat monoolein crystals, and diolein crystals in both systems. As a result, neither the HOCO nor the canola glycerolysis products displayed high temperature crystallization peaks. This means that when stored at 5° C. monoolein and diolein crystal growth would have occurred from a small number of nucleation sites, resulting in the very large crystal structures seen within these systems.

Cottonseed, rice bran, and soybean glycerolysis products each possessed similar needle-like morphologies. The cottonseed and rice bran systems showed relatively similar crystallization behaviours (proportionally large high-temperature crystallization peak with an onset just below 20° C.), not shared by the soybean glycerolysis product. However, all three oils contained low levels of oleic acid relative to palmitic acid (their SFA of highest proportion). Cottonseed, rice bran, and soybean had oleic:palmitic ratios of 0.77, 2.22, and 2.04, respectively. Sesame oil had the next lowest ratio (3.97). Rice bran oil did have a substantially higher overall oleic acid content (41.6%) compared to cottonseed (18.2%) and soybean (21.6%) oils, which may have affected the crystal composition, given that the rice bran system had a greater long-spacing (47.26 Å) compared to the cottonseed (46.15 Å) and soybean (46.94 Å) systems. But this evidently did not affect crystal morphology. Furthermore, these long-spacings demonstrated that monopalmitin was the primary molecular species in the MAG crystals of each system and XRD did not indicate the presence of DAG crystals, both factors would have contributed to the similar microstructures. Meanwhile, the peanut glycerolysis product, which was the only other system with an XRD pattern indicating the network was composed of only MAG crystals, had a long-spacing (49.46 Å) to indicate monopalmitin was not the primary species within the crystalline material. Peanut oil contained 58.4% oleic acid along with 18.8% SFAs, of which palmitic acid represented only half (9.4%). MAGs containing oleic acid and more importantly, long-chain SFAs unique to peanut oil, therefore played an important role in determining the properties of the peanut glycerolysis product and led to a high crystallization onset temperature, numerous nucleation sites, and small crystals.

Furthermore, tigernut and olive systems contained similar platelet-like crystals with similar MAG crystal compositions. This is evident from their similar long-spacings (47.58 and 48.00 Å, respectively). The fatty acid compositions of tigernut and olive oil share some similarities. Both contain high levels of oleic acid (68.1% and 75.1%, respectively) along with moderate levels of SFAs (20.8% and 14.1%, respectively). Evidently, the higher oleic acid and lower saturated fatty acid contents of the olive system resulted in the diolein crystals being the dominant crystal in the structural matrix of the olive glycerolysis product, while they were secondary to the MAG crystals in the tigernut glycerolysis product. This key difference likely factored into the less aggregated structure within the olive system.

While diolein crystals would generally be considered to have a positive contribution to the overall crystal network, they have perhaps reduced aggregation in the olive system. Additionally, diolein crystals may have been disruptive to the MAG crystals of the sesame network. The microstructure of the sesame glycerolysis product does not match any of the other systems tested, however, the crystallization curve for sesame resembles that of soybean, with peak positions for the sesame system shifted to higher temperatures by several degrees. These two systems also have similar XRD peak positions, except the sesame system contains a diolein peak, while the soybean system does not. Furthermore, in the sesame system, the amplitude of both the MAG and DAG peaks are low, demonstrating that although both MAG and DAG crystals were formed, neither crystal species were present in large quantities. It is possible that the secondary crystallization of small amounts of diolein in the sesame glycerolysis product may have been detrimental to the formation of MAG crystals, leading to its apparent lack of crystalline material.

Figure 9:
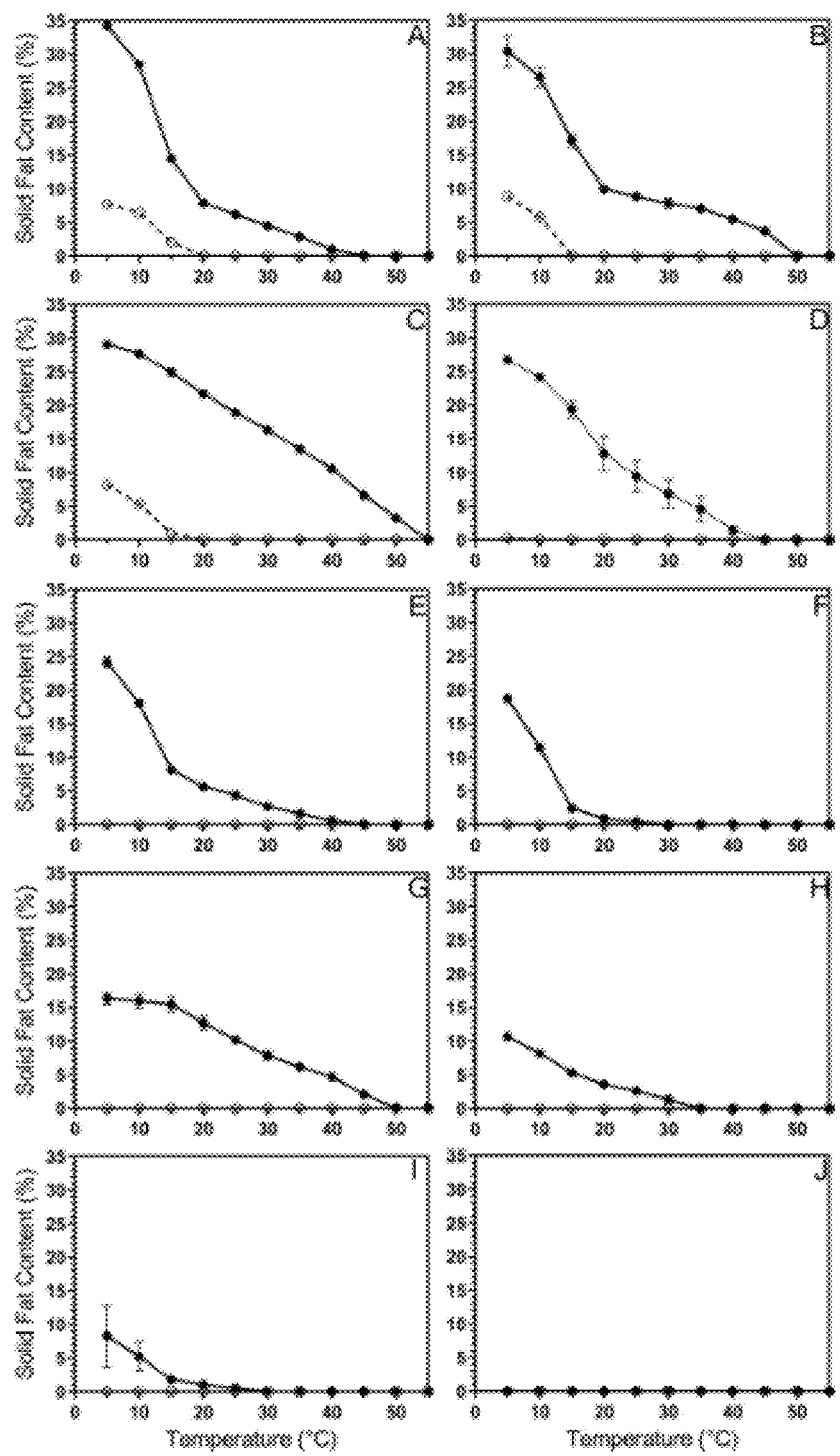
FIG. 9 illustrates solid fat content (SFC) melting profiles for glycerolysis reaction products (solid lines) and their respective oils (dotted lines) including: (A) tigernut; (B) peanut; (C) cottonseed; (D) rice bran; (E) olive (F) high oleic canola oil (HOCO); (G) soybean; (H) sesame; (I) canola; (J) high oleic algal oil (HOAO). Testing was performed after crystallization and storage at 5° C. for 1 week. Error bars represent the standard error of three replicates.

Solid Fat Content—In each of the vegetable oils studied, the changes in the crystallization behaviour of the glycerolysis reaction products resulted in increases in the solid fat content (SFC). FIG. 9 depicts the SFC-temperature profiles for each of the ten oils studied based on the data in Table 3 below.

TABLE 3

SFC of Glycerolysis reaction products

| Temp (° C.) | Tigernut | Peanut | Cottonseed | Rice Bran | Olive | HOCO | Soybean | Sesame | Canola | HOAO |
|---|---|---|---|---|---|---|---|---|---|---|
| 5 | 34.26 ± 0.18 | 30.40 ± 1.31 | 29.09 ± 0.11 | 26.72 ± 0.23 | 24.13 ± 0.46 | 18.70 ± 0.37 | 16.33 ± 0.50 | 10.65 ± 0.11 | 8.28 ± 2.66 | — |
| 10 | 28.45 ± 0.32 | 26.60 ± 0.83 | 27.69 ± 0.37 | 24.17 ± 0.16 | 18.01 ± 0.17 | 11.46 ± 0.33 | 15.93 ± 0.59 | 8.20 ± 0.17 | 5.23 ± 1.25 | — |
| 15 | 14.51 ± 0.09 | 17.16 ± 0.56 | 24.92 ± 0.20 | 19.41 ± 0.69 | 8.16 ± 0.17 | 2.43 ± 0.13 | 15.49 ± 0.67 | 5.28 ± 0.18 | 1.78 ± 0.22 | — |
| 20 | 7.85 ± 0.19 | 9.90 ± 0.22 | 21.70 ± 0.15 | 12.84 ± 1.47 | 5.65 ± 0.08 | 0.92 ± 0.25 | 12.71 ± 0.57 | 3.56 ± 0.24 | 1.03 ± 0.22 | — |
| 25 | 6.18 ± 0.08 | 8.82 ± 0.24 | 18.92 ± 0.13 | 9.43 ± 1.30 | 4.39 ± 0.21 | 0.49 ± 0.08 | 10.16 ± 0.31 | 2.62 ± 0.10 | 0.55 ± 0.13 | — |

TABLE 3-continued

SFC of Glycerolysis reaction products

| | Tigernut Oil | Peanut Oil | Cottonseed Oil | Rice Bran Oil | Olive Oil | HOCO | Soybean Oil | Sesame Oil | Canola Oil | HOAO |
|---|---|---|---|---|---|---|---|---|---|---|
| 30 | 4.51 ± 0.22 | 7.82 ± 0.42 | 16.38 ± 0.17 | 6.85 ± 1.20 | 2.68 ± 0.09 | — | 7.85 ± 0.41 | 1.33 ± 0.14 | — | — |
| 35 | 2.86 ± 0.18 | 7.04 ± 0.22 | 13.49 ± 0.25 | 4.55 ± 1.07 | 1.64 ± 0.05 | — | 6.13 ± 0.32 | — | — | — |
| 40 | 0.97 ± 0.07 | 5.48 ± 0.21 | 10.59 ± 0.30 | 1.50 ± 0.29 | 0.62 ± 0.31 | — | 4.68 ± 0.24 | — | — | — |
| 45 | — | 3.68 ± 0.08 | 6.65 ± 0.22 | — | — | — | 2.08 ± 0.21 | — | — | — |
| 50 | — | — | 3.26 ± 0.13 | — | — | — | — | — | — | — |
| 55 | — | — | — | — | — | — | — | — | — | — |

| | Tigernut Oil | Peanut Oil | Cottonseed Oil | Rice Bran Oil | Olive Oil | HOCO | Soybean Oil | Sesame Oil | Canola Oil | HOAO |
|---|---|---|---|---|---|---|---|---|---|---|
| 5 | 7.70 ± 0.09 | 8.88 ± 0.18 | 8.23 ± 0.01 | 0.28 ± 0.03 | — | — | — | — | — | — |
| 10 | 6.46 ± 0.25 | 5.76 ± 0.15 | 5.31 ± 0.29 | — | — | — | — | — | — | — |
| 15 | 2.06 ± 0.19 | — | 0.98 ± 0.25 | — | — | — | — | — | — | — |
| 20 | — | — | — | — | — | — | — | — | — | — |
| 25 | — | — | — | — | — | — | — | — | — | — |
| 30 | — | — | — | — | — | — | — | — | — | — |
| 35 | — | — | — | — | — | — | — | — | — | — |
| 40 | — | — | — | — | — | — | — | — | — | — |
| 45 | — | — | — | — | — | — | — | — | — | — |
| 50 | — | — | — | — | — | — | — | — | — | — |
| 55 | — | — | — | — | — | — | — | — | — | — |

When crystallized and stored at 5° C. for one week, the tigernut glycerolysis product (FIG. 9A) had a SFC of 34.3%, compared to 7.7% solids in the unaltered tigernut oil. Following glycerolysis, the SFC of the peanut system (FIG. 9B) was increased from 8.9% to 30.4%, while the cottonseed system (FIG. 9C) underwent an increase from 8.2% to 29.1%. The next highest SFC was observed for the rice bran glycerolysis product (26.7%; FIG. 9D). This was the last of the samples tested in which there was crystalline material in the starting oil (0.3%). Next, the olive glycerolysis product (FIG. 39E) had a SFC of 24.1%. SFC values of 18.7%, 16.3%, 10.7%, and 8.3% were observed for the HOCO (FIG. 9F), soybean (FIG. 9G), sesame (FIG. 9H), and canola (FIG. 9I) glycerolysis products, respectively. FIG. 9J depicts HOAO oil before and after glycerolysis. As mentioned earlier, the HOAO glycerolysis product did not possess any solids at 5° C. despite the increase in crystallization temperature as measured through DSC.

It has been determined that the saturated fatty acid (SFA) content and the oleic-linoleic (monounsaturated-polyunsaturated) fatty acid (MUFA:PUFA) ratio of MAGs and DAGs affected the SFC of model lipid systems. In the present study, it is evident that these characteristics both factored into the SFC of the glycerolysis products. The SFC of the cottonseed system was high due to a high SFA content (27.5%), even while the MUFA:PUFA ratio was low (0.35). Meanwhile, the tigernut and peanut systems displayed higher SFC values (5° C.) than the cottonseed system even though they contained lower levels of SFAs (20.8% and 18.8%, respectively). This highlights the importance of the MUFA:PUFA ratio, as ratios within tigernut oil (6.14) and peanut oil (2.73) were greater than in cottonseed oil. This is again exemplified by a comparison with the rice bran system, which had a higher SFA content (23.3%), but a lower SFC at 5° C. than tigernut and peanut, because rice bran oil had a MUFA:PUFA ratio of only (1.20). Furthermore, olive oil had the highest MUFA:PUFA ratio (7.62) but contained only 14.1% SFAs and did not achieve a SFC as high as the rice bran system. This demonstrates the importance of both SFAs and the MUFA:PUFA ratio. HOCO had a low SFA content (6.9%) paired with a relatively high MUFA:PUFA ratio (3.59), which allowed this system to achieve a marked increase in SFC. Evidently, the MUFA:PUFA ratio of canola oil (2.12) was not high enough to substantially boost the SFC of the canola system even though the SFA content (7.1%) was similar to HOCO. In this situation, individual PUFA contents may have been a factor. The only system comparison that could not be explained by the SFAs and MUFA:PUFA ratio was between soybean and sesame. These two systems contained identical SFA contents (15.9%), while sesame had a greater MUFA:PUFA ratio (0.89 vs 0.35). However, the SFC of the soybean system is 16.3%, while the sesame glycerolysis product only achieved 10.7%. This again suggests that crystallization was inhibited in the sesame system. To summarize, when the MUFA:PUFA ratio was low, the increase in SFC above what would be expected from the SFA contribution alone was also small. A high MUFA:PUFA ratio allowed the SFC to rise to a value much greater than simply what the SFAs contribute. However, this did not always hold true at low SFA contents. This demonstrates that SFAs and oleic acid contribute to the SFC of the lipid systems (at 5° C.) with the contribution of oleic acid being greatest when the PUFA content is at a minimum. Lower PUFA concentrations result in less dilution of the oleic acid containing species, thereby minimizing the reduction in their crystallization points.

As the sample temperature was increased and the SFC decreased, two distinctive SFC-temperature profiles were evident. In the first scenario, the glycerolysis products underwent a two-segment decrease, with substantial decreases in SFC as the sample temperature was increased from 5° C. to 20° C., before a gradual decrease as the temperature was increased further. The other SFC-temperature profile depicted a gradual decrease in SFC throughout the entire temperature range. The two-segment profile was observed for the tigernut, peanut, olive, HOCO, and canola glycerolysis products. As a result, the SFC of the tigernut system decreased from 34.3% at 5° C. to 7.9% at 20° C., while the peanut glycerolysis product decreased from 30.4% at 5° C. to 9.9% at 20° C. For the olive, HOCO, and canola systems, this rapid SFC decrease took place between 5° C. and 15° C. The olive glycerlysis product decreased from 24.1% to 8.2% and HOCO and canola systems decreased from 18.7% to 2.4% and 8.3% to 1.8%, respectively. A high oleic acid content was a commonality amongst these lipid systems. Each contained over 50% oleic acid and more than three times as much oleic acid as SFAs. Since the peanut system falls within this category, it demonstrates that even when diolein crystals were not present, the overall oleic acid content factors into the SFC-temperature behaviour. This was due to the substantial contribution of monoolein to the MAG crystals. It is for this reason that the SFC-temperature profile for the rice bran glycerolysis product appeared to transition between these two categories, since it contained the next highest oleic acid content and was the only other system with a MAG long-spacing of ≥47 Å.

Furthermore, cottonseed, soybean, and sesame glycerolysis products demonstrated gradual decreases in SFC as the temperature increased. This was most obvious with the cottonseed and soybean glycerolysis products, in which the respective SFC values decreased from 29.1% to 21.7% and from 16.3% to 12.7% as the temperature was increased from 5° C. to 20° C. The sesame system underwent a decrease in SFC from 10.7% at 5° C. to 3.6% at 20° C. While this SFC decrease was greater than that of the cottonseed and soybean systems, it was not nearly as pronounced a decrease as observed for the systems described previously. Consistent among each of these lipid systems is an oleic acid content of <40% (18.2%, 21.6%, and 39.7%, respectively). Additionally, each displayed MAG long-spacings of ≤47 Å, indicative of large amounts of monopalmitin in the MAG crystals. This resulted in the presence of less material that would melt at temperatures between 5 and 20° C., leading to a gradual decrease in SFC and a higher remaining level of solids at high temperatures (i.e., cottonseed and soybean glycerolysis products). This latter phenomenon was also observed for the peanut glycerolysis product because of the high concentration of long-chain saturated fatty acids unique to that system.

Evidently, SFAs are important in the starting oil to achieve a high SFC following glycerolysis. At least 10% SFAs are necessary, otherwise in the case of the canola system, very little solids will be present following the reaction; or the moderate level of solids produced will decrease substantially as the temperature is increased, as was the case with HOCO. Furthermore, increasing the SFA content is beneficial to the structuring ability of the reaction (i.e., increasing the SFC above that of the oil). This is true at least until the starting lipid system has a high enough SFA content that it becomes structured in its native triacylglycerol state. However, since one of the goals of these glycerolysis reactions is to reduce the saturated fat content of food products, it is most desirable to choose a lipid system that is lower in saturated fat while still able to achieve a high SFC. While cottonseed oil may still represent a desirable base oil given that its SFA content is nearly half that of palm oil, other oil systems tested showed similar or greater SFC values at 5° C., even with lower levels of SFAs. Additionally, the oleic acid content is important. When low amounts of oleic acid are present in the system, the crystals formed contain mostly SFAs and undergo a very gradual reduction in the SFC as the temperature is increased. This could potentially lead to negative sensory aspects since high levels of solids may remain at in-mouth temperatures. When oleic acid represents a portion of the crystal structure, either as monoolein or diolein, the lipid system will undergo a more substantial reduction in the SFC at the low-end temperatures, leading to a lower SFC at in-mouth temperatures. The ideal situation, which is to achieve a high level of solids at 5° C., that melt substantially at temperatures less than that of the mouth, is achievable when moderate amounts of SFAs (14%-25%) are present in the oil system along with high levels of oleic acid (>60%).

Applications in Food—The tigernut glycerolysis product had the highest SFC when measured at 5° C., a property which is very important for the structure within a variety of food applications. In addition, this system demonstrated a two-segment SFC-temperature profile with a pronounced reduction in SFC with respect to temperature. These characteristics make the tigernut glycerolysis product an ideal candidate for refrigerated soft-tub margarine and fat spreads.

A margarine product was successfully produced with the tigernut glycerolysis product. Margarine samples were prepared in 100 g batches from tigernut oil following glycerolysis performed under optimal reaction conditions. The oil phase represented 81 wt % of the margarine. Sodium chloride (1.8 wt %) and 0.1 wt % potassium sorbate (Sigma-Aldrich) were dispersed in water (17.1 wt %). The water phase was added to the oil phase and mixed with an immersion blender until completely homogenous. Samples were then spread on a stainless-steel tempering table maintained at 5° C. and sheared for several minutes with a plastic bench scraper in order to induce crystallization. Margarine samples were then stored at 5° C. for 1 week.

The experimental margarine had a high stability demonstrating minimal phase separation after 10 months storage at 5° C. The microstructure of the tigernut margarine sample after 10 months storage was shown to have several larger droplets of water within the sample, as would be expected after 10 months time, however, most of the water droplets visible within the fat crystal network are less than 20 μm in diameter.

Figure 10:
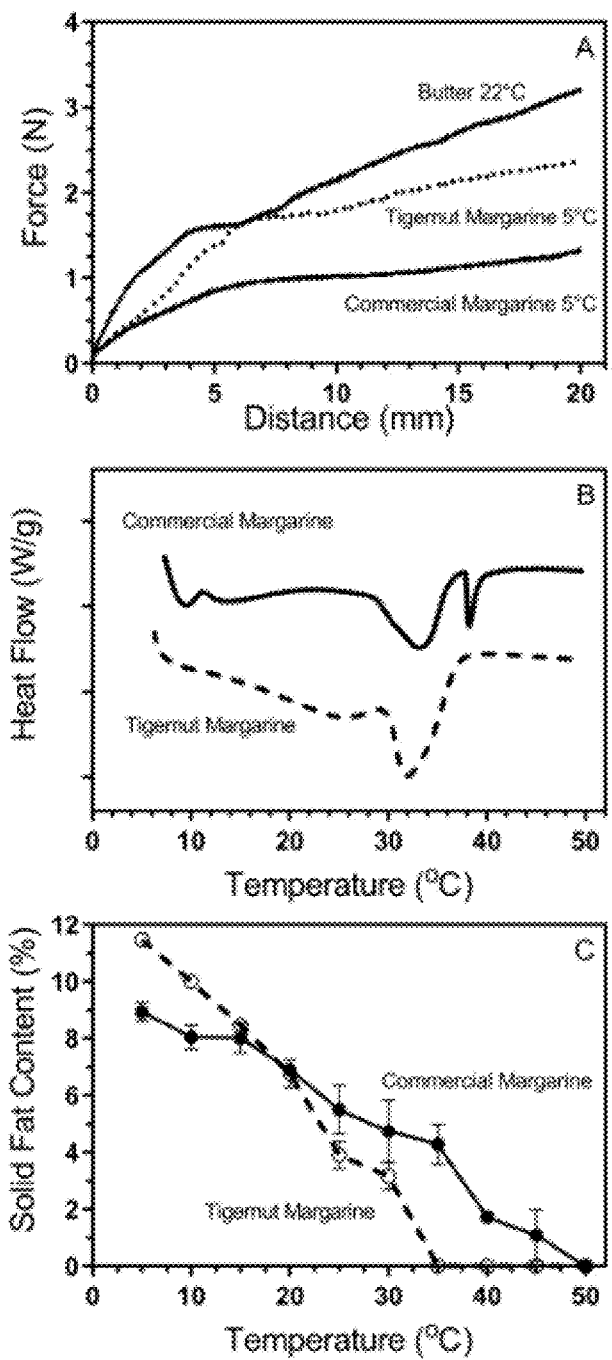
FIG. 10 illustrates (A) back extrusion force deformation profiles for butter, tigernut glycerolysis product margarine and commercial margarine; (B) differential scanning calorimetry and (C) solid fat content melting profiles for margarine produced with tigernut glycerolysis product (dotted line) and a commercially available soft-tub margarine (solid line).

FIG. 10A shows the force-deformation profiles for commercially available butter and soft-tub margarine, along with that of the margarine prepared with the tigernut glycerolysis product. Testing was performed at the expected temperatures of use for each sample; butter at 22° C. (room temperature) and the soft-tub and experimental margarines at 5° C. (refrigeration temperature). The margarine formulated with the tigernut glycerolysis product demonstrated a force-deformation profile similar to those obtained for commercially available soft-tub margarine and butter, each displaying a smooth force-deformation curve without any stress accumulation, characteristic of plastic flow behaviour. Examining the force required to deform the material (firmness), butter was firmer than the soft-tub margarine. More importantly, it is evident that the deformation curve of the experimental margarine lay in between the commercially available products, performing more similarly to room temperature butter. These results indicate that tigernut oil structured through glycerolysis can be used to prepare margarine with plastic behaviour similar to that of commercially available soft-tub margarine and butter, while producing a margarine product with a firmness that more closely resembles that of butter.

The melting profiles of the experimental margarine produced with the tigernut glycerolysis product are pictured in FIG. 10B. DSC thermograms demonstrated a gradual melting of the experimental margarine product from the 5° C. start temperature until approximately 26° C. A distinctive melting peak was then visible at approximately 32° C. This melting behaviour is very promising for the eating characteristics of the margarine, as the melting peak occurred at a temperature just below that which is typically associated with in-mouth temperatures.

FIG. 10C depicts the SFC-temperature profile. A gradual reduction in the SFC of the margarine was seen with increasing temperature. 3.2% solids remained when the margarine samples were tested at 30° C. (just below the temperature of the mouth) and 0% solids were present when the sample was measured at 35° C. Therefore, no solids remained at in-mouth temperatures, thereby demonstrating that the margarine formulated with the tigernut glycerolysis product yielded nearly optimal melting characteristics. Interestingly, the commercially available soft-tub margarine had a lower SFC when measured at 5° C., which explains the lower firmness compared to the tigernut margarine. In addition, the SFC of the commercial margarine decreased much more slowly with increasing temperature and over 4% solids remained at 35° C. The DSC melting profile confirmed the presence of a melting peak just below 40° C. This indicates that edible oils structured through glycerolysis, can produce margarines with proper melting characteristics, without a lingering waxy mouthfeel.

Thus, we have demonstrated that glycerolysis is a viable means of structuring plant-based oils with potential to be used in the production of margarine and spreads. Using these structured oils would improve the fatty acid profile and sustainability of the product as palm oil would no longer be a required ingredient. Additionally, hydrogenated oils are not required further increasing the advantages of this product.

The potential oils which could be structured through glycerolysis and used for margarine and spread production do not stop at tigernut oil. Many other oils that contain an intermediate SFA content and high oleic acid concentration (e.g. sesame, peanut and rice bran) represent potential options to be used for margarine formulation. The versatility of the glycerolysis process for improving the functionality of oils means that the oil of many oilseed crops already in production for other purposes around the world could be used in a greater variety of food applications. This would reduce the need to produce more palm oil to meet demand for functional oils, while improving the healthfulness of food products. Besides spreads and margarines, partially crystalline oils, such as the HOCO, soybean, sesame, and canola glycerolysis products, could be used as a self-emulsifying system due to the high MAG content. Moreover, the presence of crystals could help stabilize emulsions, both W/O and O/W via Pickering mechanisms without requiring added emulsifiers.

Furthermore, using glycerolysis to structure oils improves the overall healthfulness of the system. In addition to the healthier fatty acid profiles of liquid oils structured through glycerolysis compared to palm oil or other means of improving the functionality of a lipid system (i.e., SFA addition). Glycerolysis-structured oils also bring with them the health benefits that have been associated with the consumption of DAGs in place of TAGs. Due to differences in the metabolic pathway of 1,3-DAGs compared to TAGs, consumption of DAGs rather than TAGs has been shown to reduce body fat stores and serum TAG levels along with low-density lipoprotein cholesterol and total cholesterol levels. This makes glycerolysis-structured oils a healthy, functional fat source.

Conclusions

This research has shown that through glycerolysis, the SFC of liquid vegetable oils can be increased, structuring them into solid fats without altering their fatty acid profile. The effectiveness of glycerolysis at structuring oils is dependent on the fatty acid composition of the liquid oil. The potential structuring power of the glycerolysis reaction is greatest when SFAs are present at intermediate concentrations (14-25%) and the oleic acid content is high. This oil composition was also beneficial to the melting characteristics of the structured system. When used to formulate margarine, glycerolysis-structured oils provide a solution to the lack of plasticity often observed with fat mimetics and when the appropriate oil system is used, namely tigernut oil, solves the melting behaviour issues commonly experienced with wax-based oleogel systems. In some cases, margarine prepared with glycerolysis-structured oils perform better than commercial margarine prepared with palm oil. Using plant-based oils structured through glycerolysis, provides a sustainable way to reduce demand for palm oil, which would help to end further habitat and environmental destruction throughout the world's tropical regions. Glycerolysis-structured oils offer a healthful solution to blending liquid oils with high SFA fats to improve the functionality of an oil.

Example 4—Phase Behavior of Mixtures of Pure Monoacylglycerols and Diacylglycerols The impact of monoacylglycerol and diacylglycerol content on a glycerolysis structured fat was determined.

Materials and Methods

Materials—Diolein (>99% purity), 1-palmitoyl-3-oleoyl-glycerol (>98% purity), 1-oleoyl-2-palmitoyl-glycerol (>98% purity), 1-palmitoyl-2-oleoyl-glycerol (>98% purity), 1-monopalmitin (>99% purity), 1-monoolein (>99% purity), and 1-monolinolein (>99% purity) were purchased from Larodan (Larodan Research Grade Lipids; Solna, Sweden). Monopalmitin and monostearin obtained from Kerry Group (Tralee, Ireland) were used to investigate the phase behavior of monopalmitin+monostearin mixtures.

Mono- and Diacylglycerol Mixtures—Several mixtures were investigated. 1-monoolein was mixed at varying proportions with (i) 1-monolinolein and (ii) 1-monopalmitin, individually. Diolein was mixed with various concentrations of (iii) 1-monoolein and (iv) 1-monopalmitin, individually. A palmitoyl-oleoyl-glycerol isomeric blend was employed containing approximately equal amounts of 1-oleoyl-2-palmitoyl-glycerol and 1-palmitoyl-2-oleoyl-glycerol representing 30-40% (w/w) with 1-palmitoyl-3-oleoyl-glycerol present at 60-70% (w/w), to better represent the isomeric equilibrium present in food systems due to acyl migration. This palmitoyl-oleoyl-glycerol blend was mixed with various concentrations of (v) diolein and (vi) 1-monopalmitin, individually. In addition, a blend of diolein and 1-monopalmitin, such that 1-monopalmitin was present at 6.6-10.1% (w/w) relative to the diolein, was mixed with varying amounts of (vii) 1-monoolein and the (viii) palmitoyl-oleoyl-glycerol isomeric blend, individually.

Differential Scanning calorimetry—DSC was used to study the melting behavior of mixtures of pure monoacylglycerols and diacylglycerols. Mono- and diacylglycerol mixtures were weighed into aluminum crucibles and hermetically sealed prior to testing. Samples were heated to 100° C. and held for 30 min to ensure that the crystal structure was completely melted. Subsequently, samples were cooled, at a rate of 5° C./min, to −30° C. and held for 30 min. Finally, samples were heated to 80° C. at a rate of 5° C./min. This procedure was performed in triplicate for each of the blends examined.

Monopalmitin+Monostearin Mixture Analysis—Monopalmitin and monostearin were weighed at varying proportions into aluminum crucibles and hermetically sealed prior to testing. In the DSC (DSC 1 Star System), samples were heated to 100° C. and held for 30 minutes. Crystallization was then performed at rates of 20, 10, and 1° C./min reducing the sample temperature to 5° C. This temperature was maintained for 10 min before heating the samples at 5° C./min to 80° C. These samples were subsequently stored for 1 week at 20° C. before being heated in the same manner.

X-Ray Diffraction—X-ray diffraction (XRD) spectra of similar monopalmitin+monostearin mixtures, 2 min after crystallization at 5° C. and after 1 week of storage at 20° C., were obtained with a Multiflex powder X-ray diffractometer (Rigaku MSC Inc.; Toronto, ON, Canada). A copper X-ray tube (CuKα1; λ=1.54 Å) was used as the X-ray source. Spectra were acquired at either 5° C. or 20° C. in the 2θ 1-35° diffraction angle region at a 0.5° min' acquisition speed with a divergence and scattering slit of 0.5°, and a 0.3 mm receiving slit.

Results and Discussion

In this discussion, the terms compatible and incompatible are frequently used. Within the context of this paper, compatible is used to refer to situations in which two or more partial acylglycerols displayed only one melting peak (i.e., multiple molecular species melt as one entity). Conversely, incompatible is used in reference to situations where individual melting peaks were displayed for each of the partial acylglycerol species (i.e., molecular species melt as separate entities).

Figure 11:
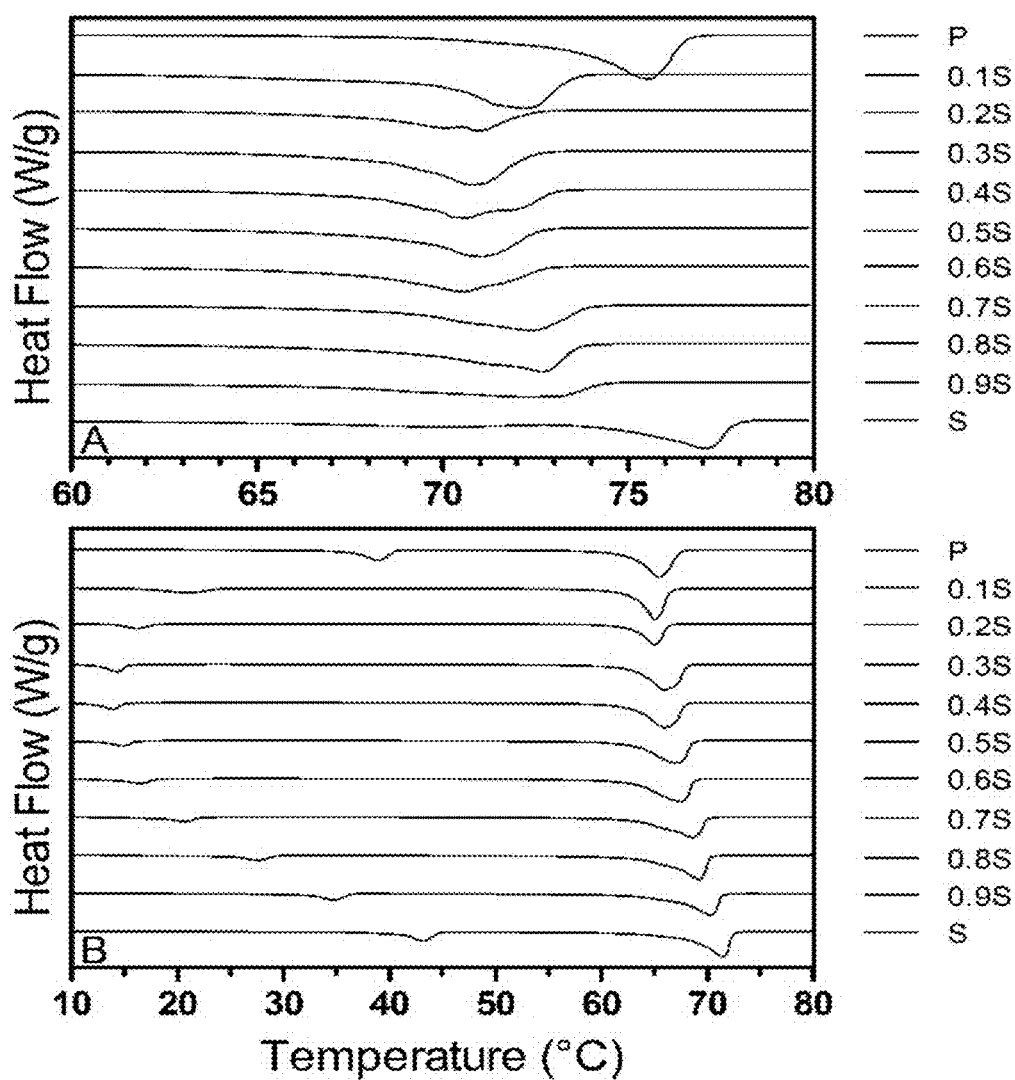
FIG. 11 illustrates differential scanning calorimetry melting profiles for monopalmitin (P), monostearin (S), and binary mixtures of the two. Prior to melting, samples were in either the (A) β polymorphic form or (B) sub-α polymorphic form.
Figure 12:
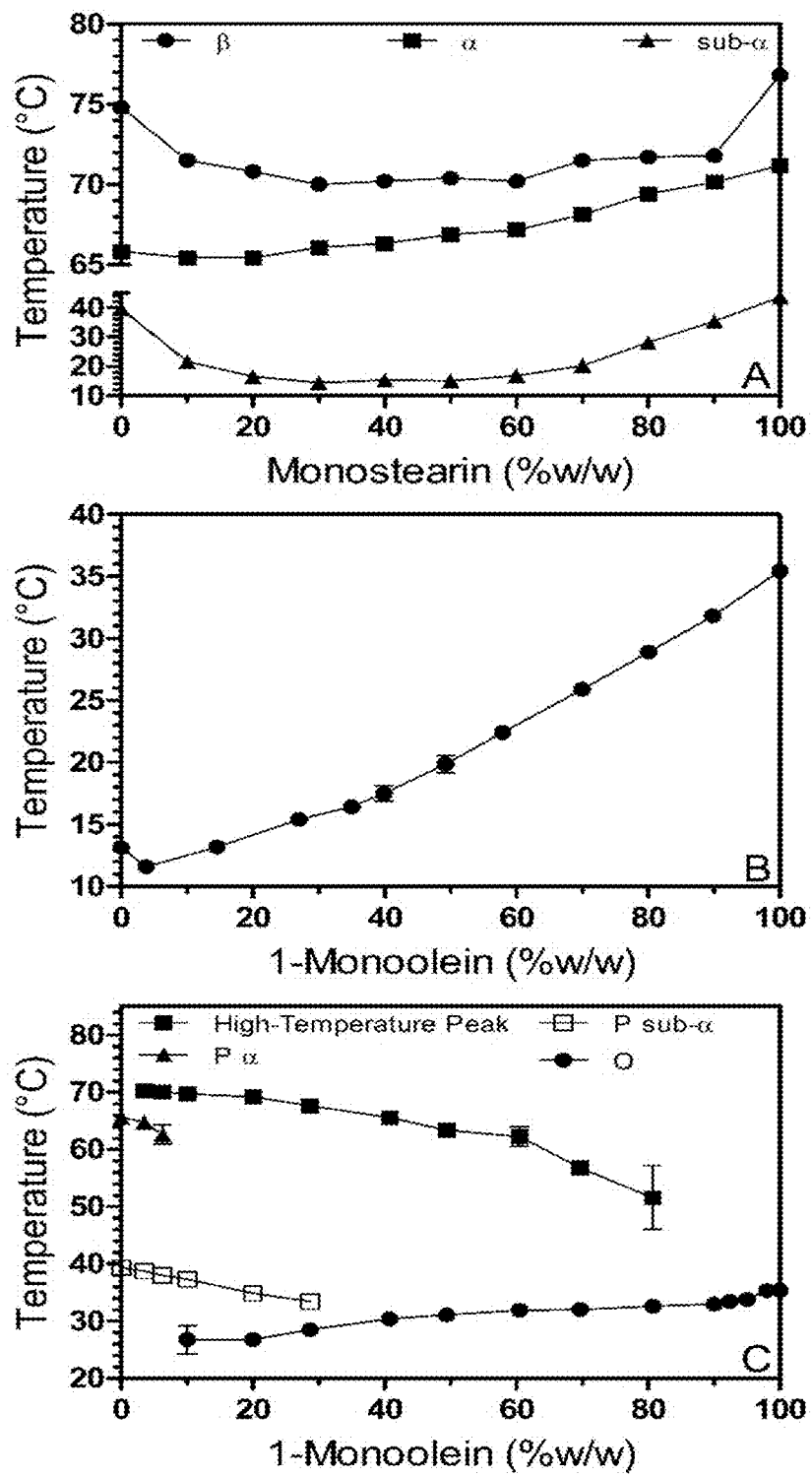
FIG. 12 illustrates peak melting temperatures for crystallized mixtures of (A) monopalmitin+monostearin, (B) 1-monolinolein+1-monoolein, and (C) 1-monopalmitin+1-monoolein. In the legend, P represents 1-monopalmitin and O represents 1-monoolein.

Monopalmitin+Monostearin—The melting behaviour of the monopalmitin+monostearin mixtures was investigated after samples were crystallized to 5° C. and held for 2 min, or stored for 1 week at 20° C. XRD analysis performed showed that crystals of the mixtures stored for 1 week at 20° C. were in the β polymorphic form, while after 2 min storage at 5° C., samples were in the sub-α form. The melting behavior of the binary mixtures differed depending on whether the mixture was in the metastable (sub-α) or stable (β) polymorphic form. FIG. 11 shows the DSC melting thermograms of the mixtures in the β. (FIG. 11A) and sub-α (FIG. 11B) polymorphic forms. FIG. 12A shows the DSC peak melting temperatures for the monopalmitin+monostearin mixtures.

In the β polymorphic form, binary mixtures showed lower melting points at each of the monostearin concentrations tested relative to both pure monopalmitin and pure monostearin. A single melting peak at each monstearin-monopalmitin proportion was observed in the β polymorphic form. However, upon close examination of the DSC thermograms in FIG. 11A, it is evident that in many cases there appear to be two melting peaks side-by-side or combining to form one broad peak, and had melting points which were lower than that of the pure constituents. This is characteristic of a eutectic mixture. Lower melting temperatures obtained may also be due to the presence of both sn-1 and sn-2 MAG isomers in both the monopalmitin and monostearin used in our study. In the present study, neat monopalmitin, crystallized in the β polymorphic form, had a melting point of 74.8° C., while the neat β form of monostearin had a melting point of 76.8° C. (FIG. 12A). The mixture containing just 10% monostearin in monopalmitin displayed a melting peak at 71.5° C. Conversely, the mixture containing 10% monopalmitin in monostearin displayed a melting peak at 71.8° C. This demonstrated that each of the mixtures had melting points that were substantially lower than that of both the pure MAG species.

When the binary mixtures were in the metastable state, two peaks were observed. The low-temperature peak corresponds to the sub-α polymorph, while the high-temperature peak corresponds to the α polymorph. Pure monopalmitin in the α form had a melting peak temperature of 65.8° C. This did not change much (65.4° C.), in the presence of 10% and 20% monostearin. At higher concentrations of monostearin, the melting point of the binary mixture in the a polymorphic state steadily increased to 71.2° C. (pure monostearin). The addition of monostearin to the mixture produced a very similar trend in the sub-α peak temperature to that of the β peak, albeit at lower temperatures. In pure monopalmitin, the sub-α melting peak was 39.5° C. This was reduced to 21.6° C. with just 10% monostearin and continued to decrease, reaching a minimum of 14.5° C. at 30% monostearin. Once monostearin was present at >50%, the temperature of the sub-α peak began to increase, ultimately reaching 43.5° C. for pure monostearin.

Since commercial MAGs often contain mixtures of monopalmitin and monostearin, this eutectic phase behavior (in the β form) may have large consequences on their structuring power. Given that small amounts (<10%) of monopalmitin in monostearin, or vice versa, lead to large changes in the melting properties of the eutectic mixture, if the compositions of these two MAGs are not closely controlled, large inconsistencies in product behavior could arise. In addition, because of the difference in melting behavior of this binary mixture depending on whether the mixtures are melted from the sub-α or β polymorphic form, the melting point of mixtures would greatly increase upon a sub-α to β transformation. For example, in the case of pure monostearin, a sub-α to β transformation will cause the melting temperature to increase by 5.6° C. (71.2-76.8° C.), compared to 1.6° C. (70.2-71.8° C.) and 2.3° C. (69.4-71.7° C.) increases for 10% monopalmitin/90% monostearin and 20% monopalmitin/80% monostearin mixtures, respectively. This further highlights the importance of carefully controlling the composition of the two MAGs.

1-Monolinolein+1-Monoolein—In the current set of experiments, pure 1-monoolein and 1-monolinolein each showed only one crystallization and melting peak. Furthermore, 1-monolinolein and 1-monoolein co-crystallized at each of the binary mixture concentrations tested, forming a single peak (FIG. 12B). However, very low concentrations of 1-monoolein in 1-monolinolein, below 4%, decreased the melting point from that of pure 1-monolinolein slightly. Pure 1-monolinolein crystals had a melting point of 13.1° C. This was depressed to 11.6° C. upon incorporation of 3.8% 1-monoolein. Further increases in the 1-monoolein content produced a steady increase in the melting point up to 35.4° C. (pure 1-monoolein). The ability of these MAG species to co-crystallize likely results from structural similarities between the molecules. Monostearin differs from monopalmitin only by the length of the fatty acid moieties, with stearic acid containing two additional methylene groups relative to palmitic acid, while 1-monolinolein differs from 1-monoolein by the presence of one additional unsaturation on the linoleic acid moiety.

1-Monopalmitin+1-Monoolein—This binary mixture demonstrated complex melting behavior. Melting peak positions for the mixtures are shown in FIG. 12C. Pure 1-monopalmitin showed a sub-α melting peak at 39.3° C. and an α melting peak at 65.6° C., while pure 1-monoolein displayed a melting peak at 35.4° C. Initially, 1-monoolein co-crystallized with 1-monopalmitin (<10.1% 1-monoolein). At these concentrations, 1-monoolein did not display a melting peak; however, the presence of the 1-monoolein did reduce the temperature of both 1-monopalmitin peaks. A peak for 1-monoolein (26.1° C.) appeared once this MAG was present at a concentration of 10.1%, indicating an incompatibility between the two components. Beyond this concentration, the sub-α peak continued to shift to a lower temperature before converging with the increasing 1-monoolein peak above a 1-monoolein concentration of 28.7%.

Figure 13:
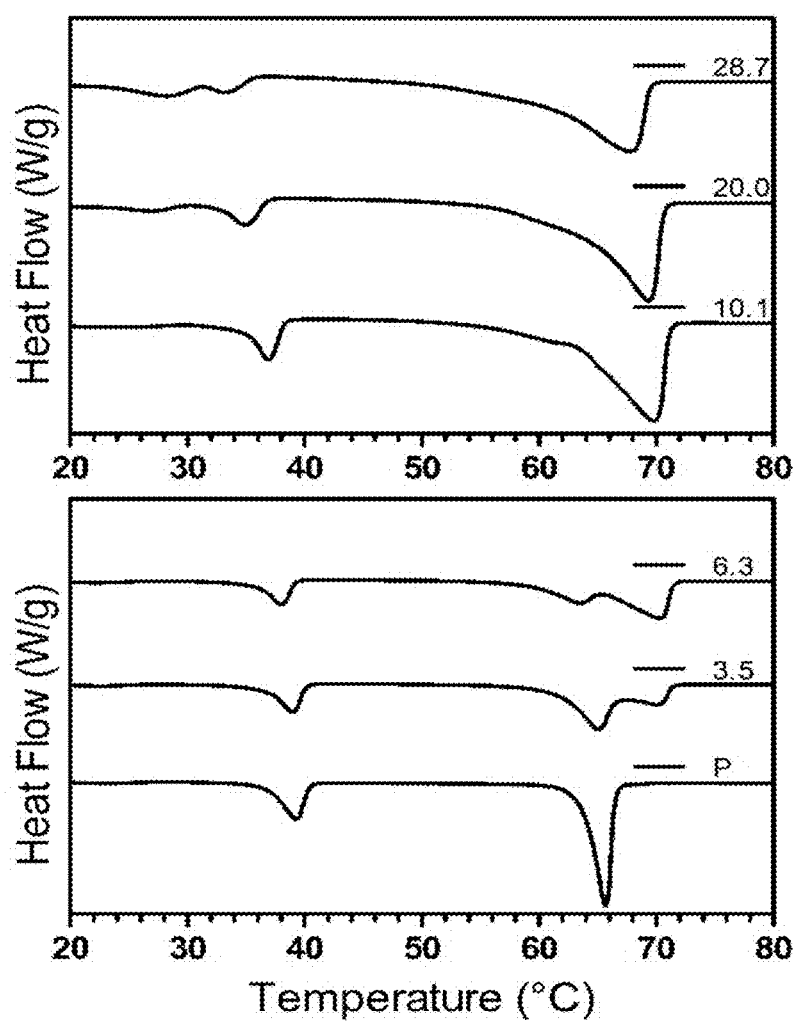
FIG. 13 illustrates differential scanning calorimetry melting profiles for pure 1-monopalmitin (P) and following the addition of 1-monoolein, such that 1-monoolein was present within the binary mixture at 3.5, 6.3, 10.1, 20.0, and 28.7% (w/w).

Interestingly, the addition of 1-monoolein resulted in the formation of a high-temperature melting peak at 70.2° C. The appearance of this peak is shown in FIG. 13 following the addition of 3.5% 1-monoolein to 1-monopalmitin. Monopalmitin in the α form melted at 66.9° C., while monopalmitin in the β' form melted at 74.6° C. These temperatures were determined through capillary melt experiments with the melting points being taken as the temperature at which the sample was completely melted. This would have resulted in a melting temperature slightly greater than that of the DSC peak temperature. While 70.2° C. is lower than 74.5° C., it is possible that this high-temperature peak was formed as a result of a portion of the 1-monopalmitin transitioning from the α form to the β' polymorphic form. When this high-temperature peak initially formed, it was smaller than the 1-monopalmitin α melting peak. However, as the 1-monoolein concentration was increased, the α melting peak shifted to a lower temperature and became less pronounced relative to the high-temperature melting peak, before eventually merging with the high-temperature peak at 10.1% 1-monoolein. Over this concentration range, the melting temperature of the high-temperature peak remained unchanged. It was only at 1-monoolein concentrations >20% that the temperature of this peak began a gradual decrease, while broadening. Even still, the high-temperature peak in the binary mixture displayed a final melting temperature greater than or equal to the pure 1-monopalmitin α melting peak temperature when 1-monoolein was present at concentrations of ≤40%. This peak eventually merged with the 1-monoolein melting peak, demonstrating co-crystallization of the two MAG species when 1-monoolein made up >80% of the mixture. It is likely that the 1-monopalmitin α melting peak temperature would have undergone a sharp decrease beyond 80.7% and merged with the 1-monoolein melting peak. This behavior is characteristic of a monotectic. Furthermore, the melting temperature of the mixture was lower than that of pure 1-monoolein and increased as the 1-monoolein content was increased.

The structural differences between 1-monopalmitin and 1-monoolein were evidently too great for the two MAGs to co-crystallize at any relative concentration. This made the melting behavior of the binary mixture particularly interesting. The higher-melting component, 1-monopalmitin, disrupted the 1-monoolein crystal network when the two MAG species co-crystallized at 1-monopalmitin concentrations <19.3%, lowering the melting temperature of the mixture from that of pure 1-monoolein. However, the addition of the lower-melting 1-monoolein increased the melting point of the 1-monopalmitin dominated mixtures, possibly due to a partial conversion of the 1-monopalmitin from the α form to the β' polymorphic form. This behavior has the potential to offer enhanced structuring capabilities in food systems.

Furthermore, it is of particular interest that the two MAG species melted as one single entity at 1-monopalmitin concentrations below 19.3%, while at greater concentrations they melted separately. This means that if a mixture of 1-monopalmitin and 1-monoolein were to be added to a TAG system for structuring purposes, a 1-monopalmitin+1-monoolein ratio of at least about 1:4 (w/w) would be required to observe the effects of 1-monopalmitin. Otherwise, the end of melt temperature of the material would not be increased. This may be further affected by 1-monolinolein, as co-crystallization of 1-monolein and 1-monolinolein was observed. It is possible that this would reduce the required amount of 1-monopalmitin necessary to observe its separate melting behavior; however, the dilution effects from 1-monolinolein would likely lower the melting point of the 1-monopalmitin crystals.

Figure 14:
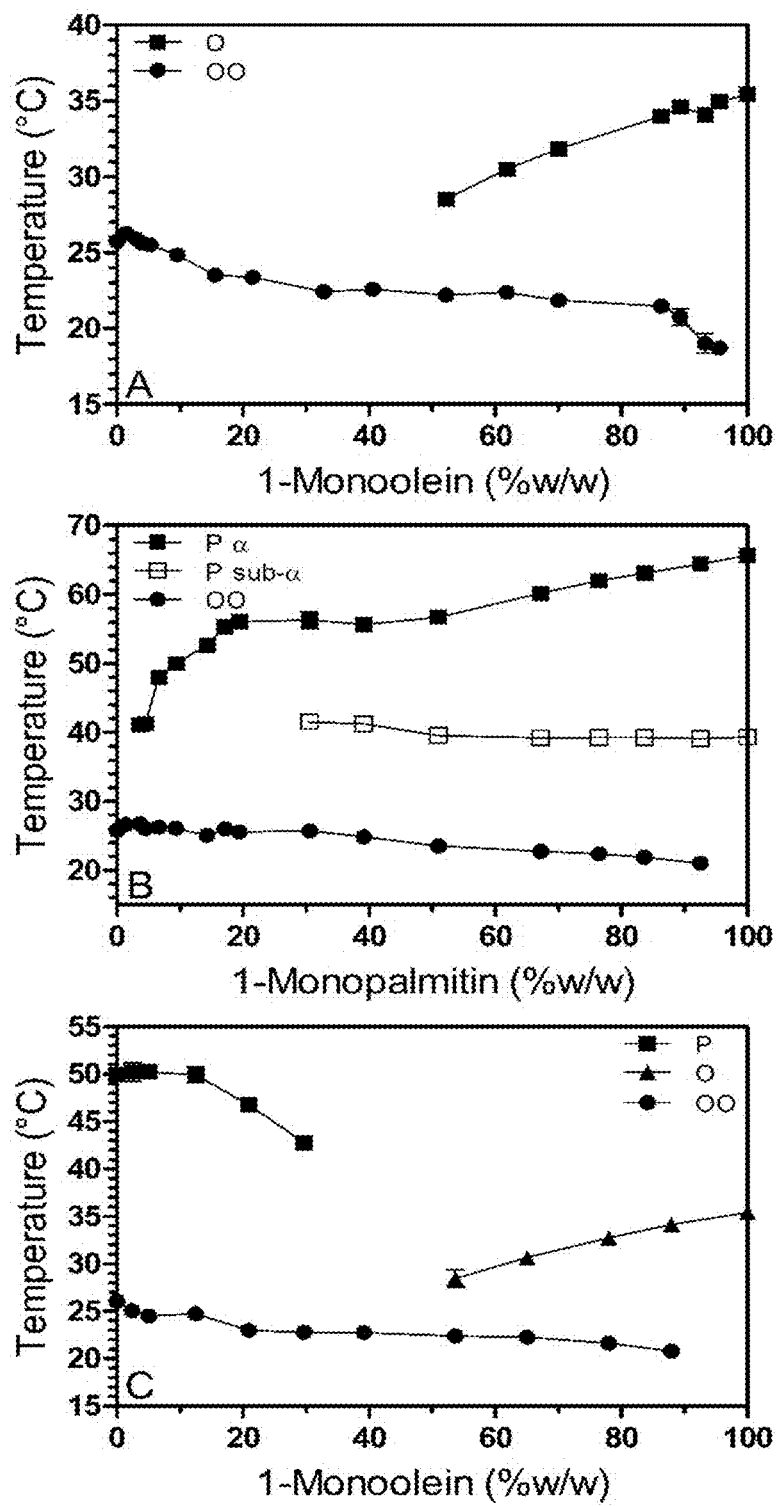
FIG. 14 illustrates peak melting temperatures for crystallized mixtures of (A) diolein+1-monoolein, (B) diolein+1-monopalmitin, and (C) diolein+1-monopalmitin+1-monoolein. In the legend, O represents 1-monoolein, OO represents diolein, and P represents 1-monopalmitin.

Diolein+1-Monoolein—The diolein used in this study was a blend of 1,2-diolein and 1,3-diolein positional isomers at unknown proportions. When crystallized, this isomeric blend produced one single melting peak at 25.7° C. (FIG. 14A). The diolein+1-monoolein phase diagram displayed three regions as the concentration of 1-monoolein was increased: (a) complete compatibility; (b) co-crystallization with melting point depression; (c) incompatibility. At 1-monoolein concentrations of <10%, diolein was completely compatible with 1-monoolein and no melting point changes relative to pure diolein were observed. Within this concentration range, the mixtures formed a single melting peak with a temperature that did not differ from that of pure diolein. Furthermore, 1-monoolein continued to co-crystallize with diolein at 1-monoolein concentrations of ≤40%, as was evident from the single melting peak observed for these mixtures. Over this range (10-40%), 1-monoolein incorporation into the diolein lattice caused decreases in the melting point of the diolein, gradually reducing the melting temperature from 25.7° C. to 22.6° C. Finally, diolein and 1-monoolein displayed incompatibility at concentrations ≥50%, where 2 distinct melting events were evident. It would be expected that just below the 1-monoolein concentration at which separate melting peaks were observed, the temperature of the 1-monoolein melting peak would have undergone a sharp increase after initially separating from the diolein melting peak. This behavior is indicative of the formation of a monotectic mixture. Furthermore, the mixture composed of 52.2% 1-monoolein in diolein displayed melting peaks at 22.2° C. and 28.5° C. In this region, the high-temperature melting peak steadily increased to 35.4° C. (pure 1-monoolein) as the 1-monoolein proportion was increased and the dilution effects from the diolein were reduced. Meanwhile, the low-temperature peak, attributed to the diolein, continued to decrease gradually to 21.5° C. at 86.3% due to freezing point depression effects. Above this, the melting point of diolein decreased sharply to 18.7° C. at 95.6% 1-monoolein. These results of this mixture are interesting in that at least 50% 1-monoolein must be present before any sign of this MAG's melting behavior can be observed. This transition from co-crystallization to incompatibility will have implications on the melting properties and structuring potential of a MAG-DAG mixture.

Diolein+1-Monopalmitin—As mentioned previously, pure diolein displayed a melting peak at 25.7° C., while 1-monopalmitin showed a sub-α peak at 39.3° C. and an α melting peak at 65.6° C. The phase diagram for this mixture showed four distinct regions. First, below 3.7%, 1-monopalmitin was able to co-crystallize with diolein, displaying a single melting peak at 26.7° C. (FIG. 14B), meaning that low amounts of 1-monopalmitin were incorporated into the diolein lattice. At higher concentrations, the 1-monopalmitin crystallized separately from the diolein, as indicated by the separate melting peaks of the diolein and 1-monopalmitin. Furthermore, the second region of the phase diagram is visible within a 1-monopalmitin concentration range of 3.7-19.4%. In this region, the α melting peak showed a strong concentration dependence, increasing from 41.1° C. to 56.0° C. The appearance of the melting peak for 1-monopalmitin and the subsequent increases in melting temperature is characteristic of a monotectic mixture. It must be noted that the sub-α melting peak could not be distinguished from the α melting peak in the 3.7-19.4% 1-monopalmitin concentration range. This was likely due to broad a peaks which were relatively close to the expected location of the sub-α peaks, rather than the lack of a transition from the sub-α to a form. It is also possible that at concentrations of 3.7% and 4.5%, 1-monopalmitin melted directly from the sub-α form. At these concentrations, the only melting peak displayed by 1-monopalmitin was at a similar temperature to that which was characteristic of the sub-α peak observed for pure 1-monopalmitin. This is similar behavior to that that was observed for monostearin in hazelnut oil (Chen et al., 2009). Evidently, in this region the crystalline 1-monopalmitin existed as a separate crystal entity embedded within the diolein network. During the melting cycle, solid 1-monopalmitin was dissolved in liquid diolein, resulting in the observed melting point reduction. Next, from a 1-monopalmitin concentration of 19.4% to 39.2%, the temperature of the α melting peak remained constant. This indicates that the solubility limit of solid 1-monopalmitin in liquid diolein was reached. It should be noted that within this region, at a 1-monopalmitin concentration of 30.6%, the sub-α (41.5° C.) and α (56.3° C.) peaks became distinguishable from one another. Finally, within the fourth region observed, increases in the 1-monopalmitin concentration above 39.2% produced a steady increase in the temperature of the 1-monopalmitin α melting peak to 65.6° C., while not affecting the melting temperature of the sub-α peak (39.3° C.). The addition of 1-monopalmitin to diolein did not appear to affect the melting temperature of diolein (24.8° C.) when 1-monopalmitin was added at ≤39.2%. However, as the 1-monopalmitin concentration was increased further to 92.6%, the melting point of diolein gradually decreased to 21.0° C. The change in the melting behavior of the mixture components indicates that at around 40% 1-monopalmitin, the 1-monopalmitin-in-diolein mixture became a diolein-in-1-monopalmitin mixture. Furthermore, relative to 1-monoolein, 1-monopalmitin had a reduced ability to co-crystallize with diolein, likely resulting from greater structural differences. Due to these incompatibilities, the melting point of a TAG mixture containing diolein can effectively be raised through the addition of 1-monopalmitin.

Monopalmitin+Diolein+1-Monoolein—It should be noted that each of these samples contained between 6.6% and 10.1% 1-monopalmitin relative to the diolein within the mixture. In the absence of 1-monoolein, the 1-monopalmitin+diolein mixture showed a major melting peak at 26.1° C., attributed to diolein co-crystallized with 1-monopalmitin. A peak at 50.0° C. was also present due to the excess 1-monopalmitin present within the mixture (FIG. 14C). Besides the peak from the excess 1-monopalmitin, this mixture behaved in a similar fashion to the diolein+1-monoolein mixture. At concentrations <53.7%, 1-monoolein co-crystallized with the 1-monopalmitin+diolein complex and caused a slight, but gradual reduction in the melting temperature, just as was observed for the diolein+1-monoolein mixture. In addition, at higher concentrations of 1-monoolein (≥53.7%), the mixture behaved in the same manner as the diolein+1-monoolein mixture with these two partial acylglycerol species producing separate melting peaks, diverging further as the 1-monoolein content increased.

The melting temperature of the excess 1-monopalmitin decreased to 42.8° C. at 29.7% 1-monoolein due to a freezing point depression effect. Moreover, at greater 1-monoolein concentrations (≥39.2%), the excess 1-monopalmitin peak disappeared, becoming completely miscible within the diolein+1-monoolein crystal network. The overall concentration of 1-monopalmitin in this sample (39.2% 1-monoolein) was 4.7%. Therefore, 1-monopalmitin displayed a higher solubility in the diolein+1-monoolein mixture than in diolein alone. This mixture demonstrated that at certain concentrations it is possible for multiple partial acylglycerol species to co-crystallize. Furthermore, once co-crystallized within the mixture, 1-monopalmitin did not affect the diolein+1-monoolein melting behavior.

Figure 15:
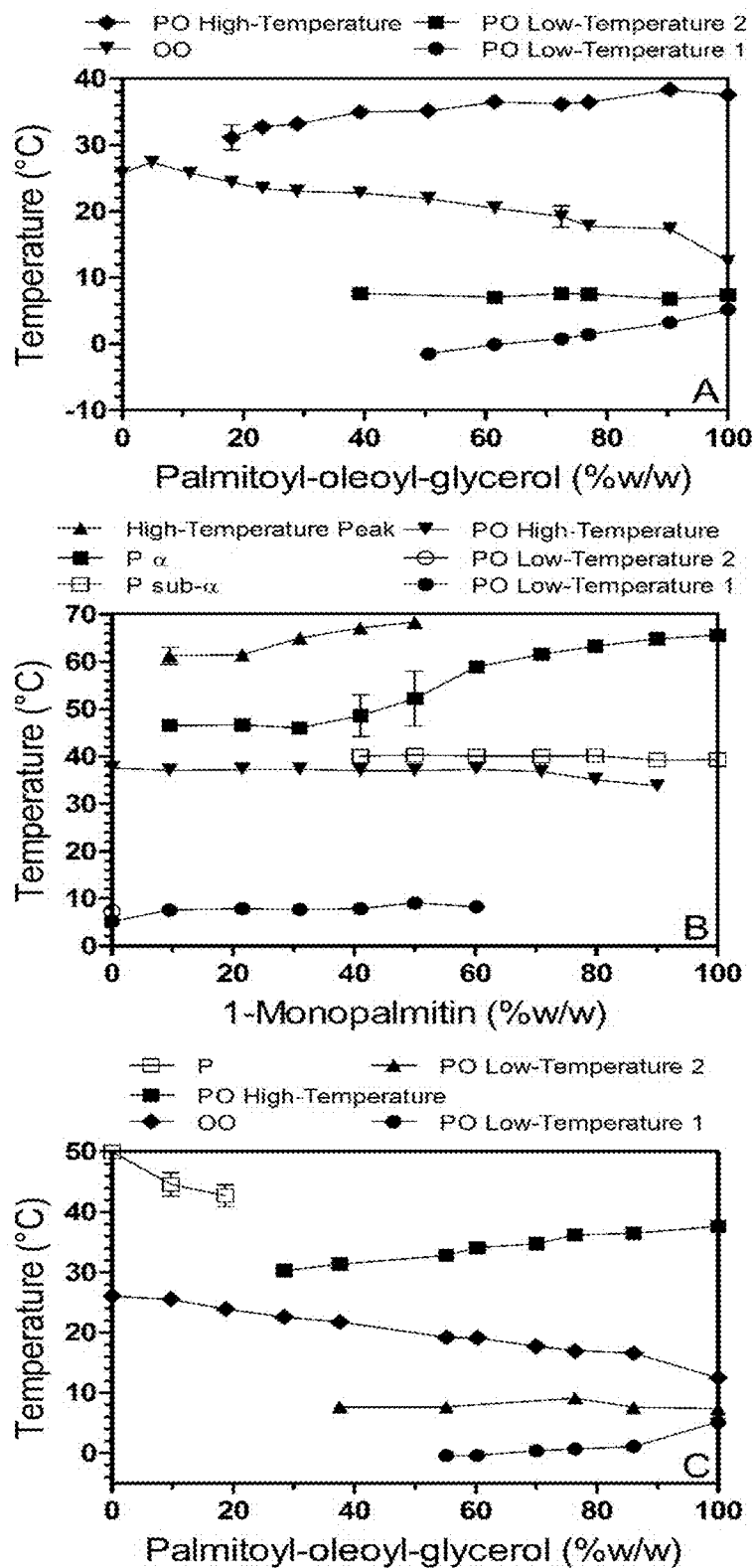
FIG. 15 illustrates peak melting temperatures for crystallized mixtures of (A) diolein+palmitoyl-oleoyl-glycerol, (B) palmitoyl-oleoyl-glycerol+1-monopalmitin, and (C) diolein+1-monopalmitin+palmitoyl-oleoyl-glycerol. In the legend, PO represents palmitoyl-oleoyl-glycerol, 00 represents diolein, and P represents 1-monopalmitin.

Diolein+Palmitoyl-oleoyl-glycerol—In these experiments, a mixture of 1-palmitoyl-3-oleoyl-glycerol (1,3-PO) and sn-1,2 isomers (1-oleoyl-2-palmitoyl-glycerol (1,2-OP) and 1-palmitoyl-3-oleoyl-glycerol (1,2-PO)) was used, with 1,3-PO present at 60-70% (w/w) in all mixtures to be representative of palmitoyl-oleoyl-glycerol (PO) in its natural isomeric ratio. The PO initially showed a high-temperature melting peak at 37.6° C. along with two smaller low-temperature melting peaks at 5.1° C. (major) and 7.3° C. (minor) (FIG. 15A). The low-temperature peaks corresponded to the two sn-1,2 isomers (1,2-OP and 1,2-PO, respectively), while the 1,3-PO was associated with the high-temperature melting peak. This demonstrated an apparent incompatibility between the positional isomers. In addition, there was a small melting peak located at 12.4° C. It is likely that this peak was caused by a small amount of diolein present within the PO samples. Meanwhile the pure diolein sample displayed a single melting peak at 25.7° C.

PO at low concentrations (≤11.2%) co-crystallized with diolein without lowering the melting temperature. In fact, the presence of 4.9% PO raised the melting temperature of the diolein peak to 27.4° C. However, at higher PO concentrations (18.1%) an incompatibility between these two DAG species arose producing a second peak at a higher temperature (31.2° C.), indicating that diolein and 1,3-PO formed a monotectic mixture. These two peaks then began to diverge as the PO concentration was increased. The temperature of the melting peak attributed to diolein began a gradual decrease to 12.4° C., while the peak attributed to 1,3-PO increased gradually to 38.3° C. at a PO concentration of 90.4%. This melting peak temperature was maintained in the absence of added diolein demonstrating that low diolein contents had no affect on 1,3-PO crystallization. Interestingly, the low-temperature peaks associated with the 1,2-PO molecules decreased in size when 9.6% diolein was present and continued to decrease as the proportion of diolein was increased, until they both ultimately disappeared once the mixture contained <40% PO. However, over this concentration range, the position of the minor low-temperature melting peak at 7.3° C. (1,2-PO) remained unchanged, demonstrating immiscibility with the mixture, while the major low-temperature melting peak, originally at 5.1° C. (1,2-OP), gradually shifted to a lower temperature, due to the dilution effects of the diolein.

The diolein+PO mixture results demonstrated that low amounts of PO (<18.1%) co-crystallized with diolein and even lower concentrations (≤11.2%) may increase the melting temperature of the mixture. Conversely, low amounts of diolein (≤9.6%) do not co-crystallize with PO but do not affect the melting properties. This means that unless at least 18.1% PO is present in a mixture with diolein, its melting peak will not be observed, meaning that PO at these lower concentrations relative to diolein would not provide any additional structuring power.

Palmitoyl-oleoyl-glycerol+1Monopalmitin—FIG. 15B depicts the melting peak positions for the mixtures of PO and 1-monopalmitin. The isomeric mixture of 1,3-PO, 1,2-

PO, and 1,2-OP showed a high-temperature melting peak at 37.6° C. (1,3-PO) along with two smaller low-temperature melting peaks at 5.1° C. (1,2-OP) and 7.3° C. (1,2-PO). Low amounts of 1-monopalmitin appeared to assist in the co-crystallization of the two sn-1,2 isomers, as the addition of 9.5% 1-monopalmitin caused the low-temperature peaks, representative of these sn-1,2 isomers to merge and form one single peak at 7.5° C. that was much smaller and broader. Furthermore, the temperature of this peak remained unchanged as the content of 1-monopalmitin was increased, concomitantly causing the peak to shrink until it eventually disappeared when >60.2% 1-monopalmitin was present. The constant melting temperature of the sn-1,2 isomers indicated that they are immiscible in the mixture.

Interestingly, the addition of 1-monopalmitin did not affect the melting temperature of the 1,3-PO peak, which remained constant at ~37° C. until 1-monopalmitin was present at 70.9%, at which point the melting temperature decreased as this peak tapered off. The concentration range in which the melting temperature of the 1,3-PO remained constant indicated that the solid-state molecular species are immiscible. Adjacent to this peak, at only a slightly higher temperature, the 1-monopalmitin sub-$\alpha$ peak became readily distinguishable above a 1-monopalmitin concentration of 30%. At lower 1-monopalmitin concentrations, this transition appeared only as a small shoulder to the 1,3-PO peak. The melting temperature of the sub-$\alpha$ peak remained constant while the peak area increased as the 1-monopalmitin concentration was increased.

The presence of 9.5% 1-monopalmitin produced two small, broad, high-temperature peaks, the first at 46.5° C. and the second at 61.3° C. It became evident at higher 1-monopalmitin concentrations that the 46.5° C. melting peak represented the $\alpha$ melting peak with a melting point of 65.5° C. for pure 1-monopalmitin, while the 61.3° C. melting peak temperature increased to 68.3° C. when the mixture contained 50.0% 1-monopalmitin, before disappearing at higher concentrations. The $\alpha$ melting peak temperature did not change across a concentration range of 9.5% to 41.0%, before undergoing a gradual increase at higher concentrations. This behavior is similar to that observed for the diolein+1-monopalmitin mixture. However, in the current mixture, the 1-monopalmitin was not added at low enough concentrations to observe either co-crystallization of the two components or a region in which the melting point of the 1-monopalmitin $\alpha$ melting peak was strongly concentration dependent. This does show that 1-monopalmitin had a lower solubility limit in 1,3-PO compared to diolein, as the region of constant $\alpha$ melting peak temperatures began at lower 1-monopalmitin concentrations. Similar to the diolein+1-monopalmitin mixture, at around 40% 1-monopalmitin, the 1-monopalmitin-in-1,3-PO mixture became a 1,3-PO-in-1-monopalmitin mixture. Furthermore, the high-temperature peak maintained a constant melting temperature between 9.5% and 31.0%, before increasing at greater concentrations. Interestingly, this high-temperature peak was sharpest at a 1-monopalmitin concentration of 50.0%, just prior to merging with the $\alpha$ peak, and subsequently disappearing. The high-temperature peak that formed was likely again the result of an $\alpha$ to $\beta'$ polymorphic transformation, with the 1,3-PO having a dilution effect causing a reduction in temperature from that which is known for 1-monopalmitin in the $\beta'$ form. This may prove useful as the 50/50 mixture of PO and 1-monopalmitin actually had a higher melting point than pure 1-monopalmitin.

1-Monopalmitin+Diolein+Palmitoyl-oleoyl-glycerol—
FIG. 15C shows that the presence of 1-monopalmitin did not change the melting behavior of the diolein+PO mixture discussed previously. The only difference in the melting profile displayed was the presence of a melting peak resulting from the excess 1-monopalmitin that did not co-crystallize with the diolein. This melting peak was observed only when PO was present at or below 18.7%, having decreased from 50.0° C. to 42.7° C. At higher PO concentrations this peak disappeared from the thermogram, demonstrating again that low concentrations of 1-monopalmitin can co-crystallize with other partial acylglycerols with no indication of its presence.

Conclusions

This research has demonstrated that complex interactions occur within mixtures of MAGs and DAGs, affecting their melting behavior. Monopalmitin and monostearin produced a eutectic mixture in the $\beta$ polymorphic form. However, at each of the concentrations tested, the melting peaks of the two species were very close together, meaning that in most cases the mixture would appear to melt as a single entity. In the $\alpha$ polymorphic form, binary mixtures of monopalmitin and monostearin displayed similar behavior to that of 1-monolinolein and 1-monoolein mixtures. Both of these mixtures showed compatibility at all concentrations tested, producing only one melting peak. In both cases, the higher melting species caused a slight reduction of the melting point of the mixture before producing an increase in the melting peak temperature. Furthermore, 1-monopalmitin and 1-monoolein formed a monotectic mixture, co-crystallizing at certain ratios. Interestingly, in this binary mixture, incorporation of the higher-melting MAG species (1-monopalmitin) into the lower-melting MAG lattice (1-monoolein) reduced the melting point of the mixture. Conversely, incorporation of the lower-melting species into the higher-melting crystals increased the melting point of the mixture. MAGs and DAGs containing the same fatty acid moieties (i.e., 1-monoolein and diolein) were shown to form monotectic mixtures, co-crystallizing over a relatively wide range of concentrations. When the fatty acids differed (i.e., 1-monopalmitin and diolein), MAGs could co-crystallize with DAGs only at very low concentrations over a narrow range of concentrations. The ability of 1-monopalmitin to co-crystallize with diolein was slightly improved through the addition of another partial acylglycerol species that was compatible with both molecules (i.e., 1-monoolein). PO did not demonstrate compatibility with 1-monopalmitin, however, similar to the effect of 1-monoolein on 1-monopalmitin, PO increased the melting point of the 1-monopalmitin, possibly through an $\alpha$ to $\beta'$ polymorphic transformation. Finally, diolein and PO formed a monotectic mixture, co-crystallizing at low diolein concentrations (<20%) without affecting the melting point of the mixture and melting as separate entities at greater concentrations. These interactions between partial acylglycerol species are an important step forward in gaining a better understanding of how MAGs and DAGs can be used for the purpose of raising the melting point of an oil for diverse applications. The transition from compatibility to incompatibility that some of these mixtures showed may prove especially useful. 1-monoolein+1-monopalmitin mixtures showed that more than 19.3% 1-monopalmitin is required before the higher melting point of 1-monopalmitin can begin to be exploited. In diolein+1-monoolein mixtures, at least 50% 1-monoolein must be present before there is any increase in the melting point, while 1-monopalmitin will have a noticeable effect on either diolein or PO at very low concentrations. Finally, at least 18.1% PO must be present in diolein before the melting point starts to increase.

Example 5— Sample Glycerolysis Plant-Based Meat Product

A plant-based meat product was prepared using various fats and oils, including glycerolysis structured fats, as described below.

Methods and Materials

Ingredients: Plant-based comminuted meat analogues were prepared in 180 g batches composed of 104.54 g water, 38.18 g texturized pea protein, 21.82 g oil/fat, 1.82 g liquid sunflower lecithin, 5.45 g pea protein isolate, 1.82 g methylcellulose, 1.82 g salt, 2.92 g potato starch, and 1.64 g flavour. For this trial, meat analogue sample batches were prepared separately using four different oil/fat phases, sunflower oil, a 50/50 (w/w) blend of coconut and sunflower oils, glycerolysis-structured tigernut oil, and glycerolysis-structured cottonseed oil. Glycerolysis reactions were performed for 48 hours, in the presence of a 1:1 glycerol:triacylglycerol (mol:mol) ratio using *Candida antarctica* lipase B as the catalyst.

Preparation: To prepare the meat analogue batter, texturized pea protein was first hydrated in water for 30 minutes. Dry ingredients (i.e. pea protein isolate, methylcellulose, salt, potato starch, and flavour) were mixed together until homogenous. Next, liquid ingredients (i.e., liquid sunflower lecithin, oil/fat) were added to the hydrated texturized pea protein in a benchtop mixer and mixed with a paddle attachment on low for 1 minute. It must be noted that the solid fats (i.e., coconut-sunflower oil blend, glycerolysis-structured tigernut oil, glycerolysis-structured cottonseed oil) were melted prior to mixing with the other liquid ingredients. The pre-blended dry ingredients were then combined with the rest of the ingredients in the benchtop mixer and mixed on low for 1 minute. 40 g of batter was weighed into 4 cm diameter molds to form patties. Three separate patties were prepared from each of the four treatments. The patties (in molds) were wrapped and refrigerated for 1 hour. Sample patties were removed from molds, weighed, and cooked in a pre-heated pan (high heat setting) until an internal temperature of 75° C. was reached (3-4 minutes per side). Cooked samples were covered and allowed to cool for 30 minutes at room temperature before analysis.

Analysis: Sample weights were recorded before and after cooking. Cook loss was determined based on the sample weight before (weight raw sample: Wr) and after cooking (weight cooked sample: Wc). Cook loss was calculated as follows: Cook Loss (%)=[(Wr−Wc)/Wr]×100%.

Texture profile analysis was performed using a texture analyzer (TA.HD. plus, Stable MicroSystems, Texture Technologies Corp.; Scarsdale, N.Y., USA) equipped with a 30 kg load cell. During texture profile analysis, samples were compressed to 25% of their original height between parallel-plate geometry during a two-cycle uniaxial compression. Several useful parameters were obtained by texture profile analysis pertaining to the sample properties. Sample hardness was taken as the maximum force recorded during the first compression. Cohesiveness is a measure of the resistance exerted by the sample during the second compression relative to the sample's ability to withstand the first compression. Springiness is a measure of how well the sample springs back to its original height following the first compression. Resilience indicates how well the sample fought to regain its original height.

Results

Values for each of these parameters are displayed in Table 1.

TABLE 1

Cook loss (%), hardness (N), springiness, cohesiveness, and resilience for each of the four oil/fat phase treatments

| Oil/Fat | Cook Loss (%) | Hardness (N) | Springiness | Cohesiveness | Resilience |
|---|---|---|---|---|---|
| SunflowerOil | 9.50 ± 1.07a | 42.27 ± 4.33a | 0.43 ± 0.02a | 0.30 ± 0.01a | 0.100 ± 0.005a |
| Coconut-Sunflower Oil | 9.05 ± 1.81a | 41.53 ± 6.60a | 0.39 ± 0.03ab | 0.27 ± 0.01b | 0.086 ± 0.003b |
| Glycerolysis-Structured Tigernut | 8.21 ± 0.52a | 37.10 ± 1.55a | 0.40 ± 0.01ab | 0.27 ± 0.01b | 0.087 ± 0.003b |
| Glycerolysis-Structured Cottonseed | 8.22 ± 0.12a | 40.77 ± 3.92a | 0.36 ± 0.01b | 0.22 ± 0.01c | 0.088 ± 0.005b |

Values indicate the mean and standard deviation of the three patties tested for each treatment. Letters represent statistical significance. Values within each column with the same letter are not statistically different.

Cook Loss: This parameter was not significantly affected by any of the lipid phases. In addition to cook loss, sample diameter was measured before and after cooking. There was no change in any of the sample diameters following cooking.

Hardness: This parameter was not significantly affected by any of these lipid phases.

Springiness: Glycerolysis-structured cottonseed oil produced samples of a significantly lower springiness compared to sunflower oil. Samples containing glycerolysis-structured cottonseed oil were not significantly less springy than the samples containing the coconut-sunflower oil blend or the glycerolysis-structured tigernut oil, while samples containing sunflower oil were not significantly springier than the samples containing the coconut-sunflower oil blend or the glycerolysis-structured tigernut oil.

Cohesiveness: Samples containing sunflower oil demonstrated a significantly higher cohesiveness value compared to the coconut-sunflower oil blend and the glycerolysis-structured tigernut oil. The cohesiveness values for the samples containing the coconut-sunflower oil blend and the glycerolysis-structured tigernut oil were not statistically different. The cohesiveness was significantly reduced when samples were formulated with glycerolysis-structured cottonseed oil.

Resilience: Samples formulated with sunflower oil were slightly more resilient than the other three treatments. Samples formulated with either glycerolysis-structured tigernut oil or glycerolysis-structured cottonseed oil demonstrated resilience values that did not differ from that of the coconut-sunflower oil blend Therefore, cook loss and sample diameter were not affected by replacing the coconut-sunflower oil blend with either glycerolysis-structured tigernut oil or glycerolysis-structured cottonseed oil. In addition, sample hardness and resilience were not affected by the substitution of the coconut-sunflower oil blend with either glycerolysis-structured tigernut oil or glycerolysis-structured cottonseed oil. Finally, substitution of glycerolysis-structured tigernut oil for the coconut-sunflower oil blend did not affect the springiness or cohesiveness.

Figure 16:
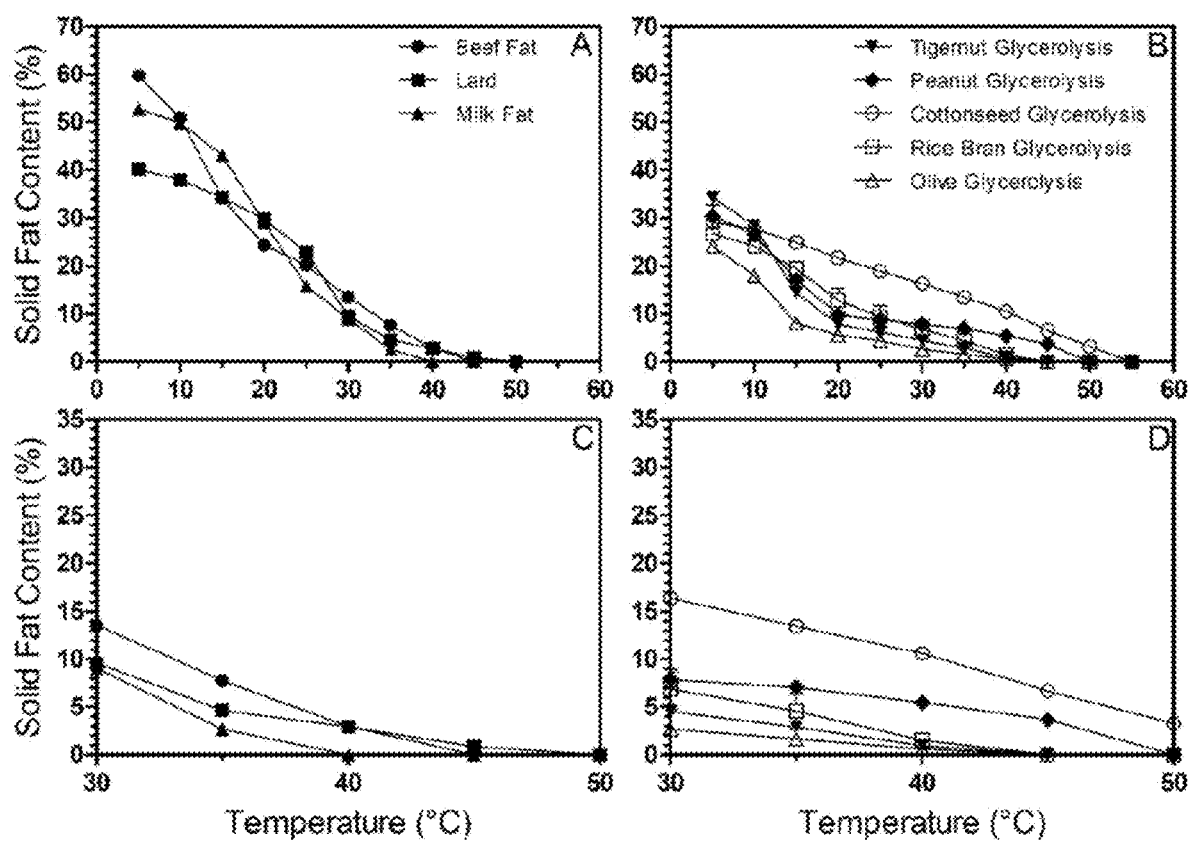
FIG. 16 graphically illustrates SFC-temperature profiles for (A) fats of animal origin and (B) various glycerolysis-structured vegetable oils, and SFC-temperature profiles at temperatures of 30° C. and above are shown for the fats of animal origin (C) and the glycerolysis-structured vegetable oils (D).

Example 6—Solid Fat Content Melting Curves of Animal Fats and Glycerolysis-Structured Oils The solid fat content (SFC) melting profiles of several glycerolysis-structured oils were compared to that of fats of animal origin. Glycerolysis reactions were performed for 48 hours, in the presence of a 1:1 glycerol:triacylglycerol (mol:mol) ratio using *Candida antarctica* lipase B as the catalyst. Fat samples were melted at 80° C. and transferred to standard glass NMR tubes (h: 180 mm; d: 9 mm). Samples were crystallized and stored at 5° C. for 1 week. Solid fat content (SFC) was measured through pulsed nuclear magnetic resonance (p-NMR) (minispec mq20, Bruker Corp.; Milton, ON, Canada). SFC was measured over a temperature range of 5-55° C. at 5° C. intervals, with a 30 min equilibration time at each temperature (AOCS Official Method Cd 16b-93). The SFC-temperature profiles of these samples are shown in FIG. 16.

The SFC-temperature profiles shown in FIGS. 16A and 16B demonstrate that the level of solids at 5° C. in beef fat and milk fat are substantially higher than that observed for any of the glycerolysis-structured oils. The lard however, showed an SFC value of 40.2% compared to the glycerolysis-structured tigernut oil which contained 34.3% solids at 5° C. This indicates that some vegetable oils structured through glycerolysis may adequately provide the level of structure to food products that would be expected from certain animal fats (i.e., lard) at refrigeration temperatures (5° C.). In addition, several of the glycerolysis-structured oils share very similar SFC values to those of the animal fats at temperatures of 30° C. and higher (FIGS. 16C and 16D). This will have implications on the in-mouth melting properties of a food product and indicates that glycerolysis-structured oils may be able to provide consumers with an in-mouth sensory experience similar to animal fats.

Figure 17:
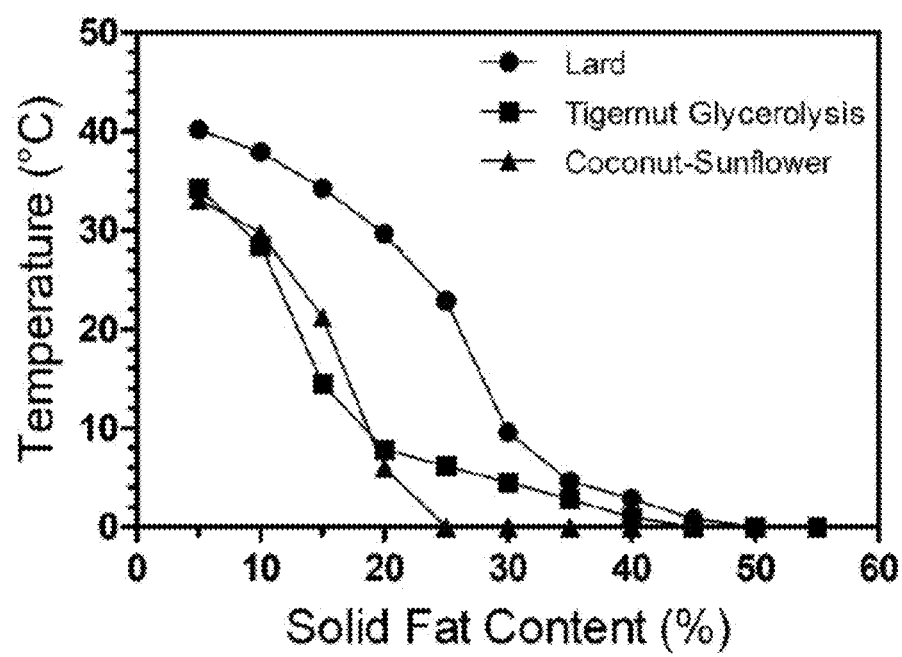
FIG. 17 illustrates SFC-temperature profiles for lard, glycerolysis-structured tigernut oil, and a 50/50 (w/w) coconut-sunflower oil blend.

An SFC-temperature profile was also obtained for a 50/50 (w/w) blend of coconut oil and sunflower oil, as coconut-sunflower blends are commonly used as the lipid material in plant-based meat analogues. FIG. 17 demonstrates that the glycerolysis-structured tigernut oil and the coconut-sunflower oil blend showed very similar SFC values at 5° C. Values were slightly less than that of the lard samples. As the temperature was increased, the SFC of the coconut-sunflower blend was reduced to 0% at a temperature of 25° C., while the glycerolysis-structured tigernut oil maintained some solid material. At temperatures above 30° C., the SFC of the lard and the glycerolysis-structured tigernut oil behaved in a very similar manner with respect to temperature.

Relevant portions of references referred to herein are incorporated by reference.

The invention claimed is:

1. An enzymatic glycerolysis method to convert a liquid oil having a first monoacylglycerol (MAG), diacylglycerol (DAG), triacylglycerol (TAG) and fatty acid composition into a structured fat, the method comprising the steps of:
   i) exposing the oil to glycerol in the presence of an enzyme catalyst under conditions sufficient to convert the triacylglycerols to mono- and/or di-acylglycerols; and
   ii) cooling the oil to yield the structured fat having a second monoacylglycerol, diacylglycerol, triacylglycerol and fatty acid composition, wherein the fatty acid composition of the structured fat is at least 95% identical to the fatty acid composition of the liquid oil.

2. The method of claim 1, wherein the enzyme catalyst is a lipase.

3. The method claim 2, wherein the enzyme is used in an amount of about 1-10% by weight of the oil.

4. The method of claim 1, wherein the amount of glycerol:TAG is about 0.5-4:1 (mol:mol).

5. The method of claim 1, wherein the amount of glycerol:TAG is about 1:1 (mol:mol).

6. The method of claim 1, which is conducted at a temperature in the range of 40-80° C. for up to about 72 hours.

7. The method of claim 1, wherein the second MAG and DAG composition is at least 20% greater than the first MAG and DAG composition, and/or the second TAG composition is at least 20% less than the first TAG composition.

8. The method of claim 1, wherein the structured fat has a solid fat content of at least about 15% at 5° C.

9. The method of claim 1, wherein the structured fat has a solid fat content of at least about 5% at 20° C.

10. A structured fat comprising 10-50% by wt monoacylglycerols (MAGs), 30-70% by wt diacylglycerols (DAGs) and 5-40% by wt triacylglycerols (TAGs), wherein the DAG content is greater than the MAG content in the structured fat, and the structured fat has a solid fat content of at least about 15% at 5° C. and/or a solid fat content of at least about 5% at 20° C.

11. The structured fat of claim 10, wherein the DAG content is at least 10% greater than the MAG content.

12. The structured fat of claim 10, which is prepared by the method of any one of claims 1 to 9.

13. A structured fat prepared by glycerolysis of a liquid oil, wherein the liquid oil comprises a first MAG, DAG, TAG and fatty acid composition, and the structured fat product comprises a second MAG, DAG, TAG and fatty acid composition, wherein the fatty acid composition of the structured fat is at least 95% identical to the fatty acid composition of the liquid oil.

14. The structured fat of claim 13, wherein the second MAG and DAG composition is at least 20% greater than the first MAG and DAG composition, and/or the second TAG composition is at least 20% less than the first TAG composition.

15. The structured fat of claim 13, comprising 10-50% by weight monoacylglycerols (MAGs), 30-70% by weight diacylglycerols (DAGs) and 5-40% by weight triacylglycerols (TAGs).

16. The structured fat of claim 13, having a solid fat content of at least about 15% at 5° C.

17. The structured fat of claim 13, having a solid fat content of at least about 5% at 20° C.

18. A food or cosmetic product comprising a structured fat as defined in claim 10.

* * * * *